United States Patent
Brunecky et al.

(10) Patent No.: US 9,249,432 B2
(45) Date of Patent: Feb. 2, 2016

(54) ENZYMES FOR IMPROVED BIOMASS CONVERSION

(71) Applicant: Alliance for Sustainable Energy, LLC, Golden, CO (US)

(72) Inventors: Roman Brunecky, Arvada, CO (US); Michael E. Himmel, Littleton, CO (US)

(73) Assignee: Alliance for Sustainable Energy, LLC, Golden, CO (US)

(*) Notice: Subject to any disclaimer, the term of this patent is extended or adjusted under 35 U.S.C. 154(b) by 0 days.

(21) Appl. No.: 13/941,754

(22) Filed: Jul. 15, 2013

(65) Prior Publication Data

US 2014/0017735 A1 Jan. 16, 2014

Related U.S. Application Data

(60) Provisional application No. 61/671,208, filed on Jul. 13, 2012.

(51) Int. Cl.

| | |
|---|---|
| *C12P 19/14* | (2006.01) |
| *C12P 7/10* | (2006.01) |
| *C12N 9/42* | (2006.01) |
| *C12N 9/14* | (2006.01) |
| *C12P 7/14* | (2006.01) |
| *C12P 19/02* | (2006.01) |

(52) U.S. Cl.
CPC .................. *C12P 7/14* (2013.01); *C12N 9/2437* (2013.01); *C12N 9/2445* (2013.01); *C12P 19/02* (2013.01); *C12P 19/14* (2013.01)

(58) Field of Classification Search
CPC .. C12N 9/2437; C12N 9/2482; C12N 9/2445; C12P 7/14; C12P 19/02; C12P 19/14
USPC .................... 435/99, 165, 209, 195
See application file for complete search history.

(56) References Cited

U.S. PATENT DOCUMENTS

| | | |
|---|---|---|
| 4,952,501 A | 8/1990 | Jasin et al. |
| 5,536,655 A | 7/1996 | Thomas et al. |
| 2010/0189706 A1* | 7/2010 | Chang et al. ................ 424/94.4 |

OTHER PUBLICATIONS

VanFossen et al., Glycoside Hydrolase Inventory Drives Plant Polysaccharide Deconstruction by the Extremely Thermophilic Bacterium Caldicellulosiruptor saccharolyticus. Biotechnology and Bioengineering, vol. 108, No. 7, 1559-1569, Jul. 2011.*
Pozzo et al., Structural and Functional Analyses of β-Glucosidase 3B from Thermotoga neapolitana: A Thermostable Three-Domain Representative of Glycoside Hydrolase. J. Mol. Biol. 397, 724-739, 2010.*
Su et al., Biochemical and mutational analyses of a multidomain cellulase/mannanase from Caldicellulosiruptor bescii. Appl. Environ. Microbiol., 2012, vol. 78 (7): 2230-2240.*
Sluiter et al., "Determination of Sugars, Byproducts, and Degradation Products in Liquid Fraction Process Samples", Laboratory Analytical Procedure, Technical Report, NREL/TP-510-42623, Issue Date Dec. 8, 2006, pp. 1-11.
Yang et al., "Classification of 'Anaerocellum thermophilum' strain DSM 6725 as Caldicellulosiruptor bescii sp. nov.", International Journal of Systematic and Evolutionary Microbiology, 2010, vol. 60, pp. 2011-2015.
Zverlov et al., "Properties and gene structure of a bifunctional cellulolytic enzyme (CelA) from the extreme thermophile 'Anaerocellum thermophilum' with separate glycosyl hydrolase family 9 and 48 catalytic domains", Microbiology, 1998, vol. 144, pp. 457-465.
Brunecky et al., "Revealing Nature's Cellulase Diversity: The Digestion Mechanism of Caldicellulosiruptor bescii CelA", Science, Dec. 20, 2013, vol. 342, pp. 1513-1516.

* cited by examiner

*Primary Examiner* — Ganapathirama Raghu
(74) *Attorney, Agent, or Firm* — John C. Stolpa

(57) ABSTRACT

Disclosed herein are enzymes and combinations of the enzymes useful for the hydrolysis of cellulose and the conversion of biomass. Methods of degrading cellulose and biomass using enzymes and cocktails of enzymes are also disclosed.

19 Claims, 16 Drawing Sheets

```
GGTTCGTTTAACTATGGGGAAGCTTTACAAAAAGCTATCATGTTTTACGAATTTCAAATGTCTGGTAAACTTCCGAATTGG
GTACGCAACAACTGGCGTGGCGACTCAGCATTAAAGGATGGTCAAGACAATGGGCTTGATTTGACAGGTGGTTGGTTTGAC
GCAGGTGATCACGTCAAGTTTAACCTTCCAATGTCATACACTGGTACAATGTTGTCATGGGCAGTGTATGAGTACAAAGAT
GCATTTGTCAAGAGTGGTCAATTGGAACATATCTTAAATCAAATCGAATGGGTTAATGACTATTTTGTAAAATGTCATCCA
AGCAAATATGTATACTATTACCAGGTTGGGGATGGAAGTAAAGATCATGCATGGTGGGGACCTGCTGAGGTTATGCAAATG
GAGAGACCTTCATTTAAGGTCACCCAAAGCAGTCCTGGATCTACAGTAGTAGCAGAGACAGCAGCTTCCTTAGCAGCAGCT
TCAATTGTTTTGAAAGACAGAAATCCCACTAAAGCAGCAACATATCTGCAACATGCAAAAGAATTATATGAGTTTGCAGAA
GTAACAAAAAGCGATGCAGGTTACACTGCTGCAAATGGATATTACAATTCATGGAGCGGTTCTATGATGAGCTTTCTTGG
GCAGCAGTTTGGTTGTATTTGGCAACAAATGATTCAACATATCTCACAAAAGCTGAGTCATATGTCCAAAATTGGCCCAAA
ATTTCTGGCAGTAACACAATTGACTACAAGTGGGCTCATTGCTGGGATGATGTTCACAATGGAGCGGCATTATTGTTAGCA
AAAATTACCGGTAAGGATATTTATAAACAAATTATTGAAAGTCACTTAGATTACTGGACTACAGGATACAATGGCGAAAGG
ATTAAGTATACACCAAAAGGATTAGCATGGCTTGATCAATGGGGTTCGTTGAGATATGCAACAACTACAGCATTTTTGGCA
TTTGTTTATAGCGATTGGGTTGGCTGTCCAAGCACAAAAAAAGAAATATATAGAAAATTTGGAGAAAGCCAGATTGATTAT
GCGTTAGGCTCAGCTGGAAGAAGCTTTGTTGTTGGATTTGGTACAAATCCACCAAAGAGACCGCATCACAGAACTGCTCAT
AGCTCATGGGCAGACAGTCAGAGTATACCTTCATATCACAGACATACATTATATGGAGCGCTTGTTGGTGGTCCAGGCTCT
GATCATAGCTACACAGATGATATAAGTAACTATGTGAACAATGAGGTTGCATGTGATTATAATGCAGGGTTTGTGGGTGCA
TTAGCAAAGATGTATCAATTGTACGGTGGGAATCCAATACCAGATTTCAAAGCTATTGAAACTCCAACAAACGACGAATTC
TTTGTTGAAGCTGGTATAAATGCATCCGGAACTAACTTTATTGAAATTAAAGCGATAGTTAATAACCAAAGTGGTTGGCCT
GCCAGAGCAACAGATAAGCTTAAATTTAGATATTTTGTTGACCTGAGTGAATTAATTAAAGCAGGATATTCACCAAATCAA
TTAACCTTGAGCACCAATTATAATCAAGGTGCAAAAGTAAGTGGACCTTATGTATGGGATGCAAGCAAAAATATATACTAC
ATTTTAGTAGACTTTACTGGCACATTGATTTATCCAGGTGGTCAAGACAAATATAAGAAAGAAGTCCAATTCAGAATTGCA
GCACCACAGAATGTACAGTGGGATAATTCTAACGACTATTCTTTCCAGGATATAAAGGGAGTTTCAAGTGGTTCAGTTGTT
AAAACTAAATATATTCCACTTTATGATGGAGATGTGAAAGTATGGGGTGAAGAACCAGGAACTTCTGGAGCAACACCGACA
CCAACAGCAACAGCAACACCAACACCAACGCCGACAGTAACACCAACACCGACTCCAACACCAACATCAACTGCTACACCA
ACACCGACACCAACACCGACAGTAACACCCAACCCCGACTCCGACACCGACCTGCTACACCAACACGAACGCCAACACCAACA
TCGACGCCGAGCAGCACACCTGTAGCAGGTGGACAGATAAAGGTATTGTATGCTAACAAGGAGACAAATAGCACAACTAAT
ACGATAAGGCCATGGTTGAAGGTAGTGAACACTGGAAGCAGCAGCATAGATTTGAGCAGGGTAACGATAAGGTACTGGTAC
ACGGTAGATGGGGACAAGGCACAGAGTGCGATATCAGACTGGGCACAGATAGGAGCAAGCAATGTGACATTCAAGTTTGTG
AAGCTGAGCAGTAGCGTAAGTGGAGCGGACTATTATTTACAGATAGGATTTAAGAGTGGAGCTGGGCAGTTGCAGGCTGGC
AAAGACACAGGGGAGATACAGATAAGGTTTAACAAGAGTGATTGGAGCAATTACAATCAGGGGAATGACTGGTCATGGATG
CAGAGCATGACGAATTATGGAGAGAATGTGAAGGTAACAGCGTATATAGATGGTGTATTGGTATGGGGACAGGAGCCGAGT
GGAGCGACACCAACACCGACAGCGACACCAGCACCGACAGTCACACCGACACCTACACCAACACCAACGTCAACACCAACT
GCTACACCAACAGCAACGCCAACACCAACACCGACGCCGAGCAGCACACCTGTAGCAGGCGGGCAGATAAAGGTATTGTAT
GCTAACAAGGAGACAAATAGCACAACAAACACGATAAGGCCATGGTTGAAGGTAGTGAACACTGGAAGCAGCAGCATAGAT
TTGAGCAGGGTAACGATAAGGTACTGGTACACGGTAGATGGGGACAAGGCACAGAGTGCGATATCAGACTGGGCACAGATA
GGAGCAAGCAATGTGACATTCAAGTTTGTGAAGCTGAGCAGTAGCGTAAGTGGAGCGGACTATTATTTAGAGATAGGATTT
AAGAGTGGAGCTGGGCAGTTGCAGGCTGGCAAGACACAGGGGAATGACTGGTCATGGATGCAGAGCATGACGAATTATGGAGCAAT
TACAATCAGGGGAATGACTGGTCATGGATGCAGAGCATGACGAATTATGGAGAGAATGTGAAGGTAACAGCGTATATAGAT
GGTGTATTGGTATGGGGACAGGAGCCGAGTGGAGCGACACCAACACCGACAGCGACACCAGCACCGACAGTGACACCGACA
CCTACACCAGCACCAACTCCAACCCCGACACCAACACCAACTGCTACACCAACACCAACGCCAACACCAACCCCAACCGCG
ACACCAACAGTAACAGCAACACCAACACCGACGCCGAGCAGCACACCGAGTGTGCTTGGCGAATATGGGCAGAGGTTTATG
TGGTTATGGAACAAGATACATGATCCTGCGAACGGGTATTTTAACCAGGATGGGATACCATATCATTCGGTAGAGACATTG
ATATGCGAAGCACCTGATTATGGTCATTTGACCACGAGTGAGGCATTTTCGTACTATGTATGGTTAGAGGCAGTGTATGGT
AAGTTAACGGGTGACTGGAGCAAATTTAAGACAGCATGGGACACATTAGAGAAGTATATGATACCATCAGCGGAAGATCAG
CCGATGAGGTCATATGATCCTAACAAGCCAGCGACATACGCAGGGGAGTGGGAGACACCGGACAAGTATCCATCGCCGTTG
GAGTTTAATGTACCTGTTGGCAAAGACCCGTTGCATAATGAACTTGTGAGCACATATGGTAGCACATTAATGTATGGTATG
CACTGGTTGATGGACGTAGACAACTGGTATGGATATGGCAAGAGAGGGGACGGAGTAAGTCGGGCATCATTTATCAACACG
TTCCAGAGAGGGCCTGAGGAGTCTGTATGGGAGACGGTGCCGCATCCGAGCTGGGAGGAATTCAAGTGGGGCGGACCGAAT
GGATTTTTAGATTTGTTTATTAAGGATCAGAACTATTCGAAGCAGTGGAGATATACGGATGCACCAGATGCTGATGCGAGA
GCTATTCAGGCTACTTATTGGGCGAAAGTATGGGCGAAGGAGCAAGGTAAGTTTAATGAGATAAGCAGCTATGTAGCGAAG
GCAGCGAAGATGGGAGACTATTTAAGGTATGCGATGTTTGACAAGTATTTCAAGCCATTAGGATGTCAGGATAAGAATGCG
GCTGGAGGAACGGGTATGACAGTGCACATTATCTGCTATCATGGTATTATGCATGGGGTGGAGCATTGGATGGAGCATGG
TCATGGAAGATAGGGAGCAGCCATGTGCACTTTGGATATCAGAATCCGATGGCGGCATGGGCATTAGCGAATGATAGTGAT
ATGAAGCCGAAGTCGCCGAATGGAGCGAGTGACTGGGCAAAGAGTTTGAAGAGGCAGATAGAATTTTACAGGTGGTTACAG
TCAGCGGAGGGAGCGATAGCAGGAGGCGCGACAAATTCATGGAATGGCAGATATGAGAAGTATCCAGCAGGGACAGCAACA
TTTTATGGAATGGCATATGAACCGAATCCGGTATATCCTGGGAGCAACACATGGTTTGGATTCCAGGCATGGTCG
ATGCAGAGGGTAGCGGAGTATTACTATGTGACAGGAGATAAGGACGCAGGAGCACTGCTTGAGAAGTGGGTAAGCTGGGTT
AAGAGTGTAGTGAAGTTGAATAGTGATGGTACGTTTGCGATACCGTCGACGCTTGATTGGAGCGGACAACCTGATACATGG
AACGGGGCGTATACAGGGAATAGCAACTTACATGTTAAGGTAGTGGACTATGGTACTGACTTAGGAATAACAGCGTCATTG
GCGAATGCGTTGTTGTACTATAGTGCAGGGACGAAGAAGTATGGGGTATTTGATGAGGGAGCGAAGAATTTAGCGAAGGAA
TTGCTGGACAGGATGTGGAAGTTGTACAGGGATGAGAAGGGATTGTCAGCGCCAGAGAAGAGAGCGGACTACAAGAGGTTC
TTTGAGCAAGAGGGTATATATACCGGCAGGATGGATAGGGAAGATGCCGAATGGAGATGTAATAAAGAGTGGAGTTAAGTTT
ATAGACATAAGGAGCAAGTATAAACAAGATCCTGATTGGCCGAAGTTAGAGGCGGCATACAAGTCAGGGCAGGCACCTGAG
TTCAGATATCACAGGTTCTGGGCACAGTGCGACATAGCAATAGCTAATGCAACATATGAAATACTGTTTGGCAATCAA
```

GSFNYGEALQKAIMFYEFQMSGKLPNWVRNNWRGDSALKDGQDNGLDLTGGWFDAGDHV
KFNLPMSYTGTMLSWAVYEYKDAFVKSGQLEHILNQIEWVNDYFVKCHPSKYVYYYQVGD
GSKDHAWWGPAEVMQMERPSFKVTQSSPGSTVVAETAASLAAASIVLKDRNPTKAATYLQ
HAKELYEFAEVTKSDAGYTAANGYYNSWSGFYDELSWAAVWLYLATNDSTYLTKAESYVQ
NWPKISGSNTIDYKWAHCWDDVHNGAALLLAKITGKDIYKQIIESHLDYWTTGYNGERIK
YTPKGLAWLDQWGSLRYATTTAFLAFVYSDWVGCPSTKKEIYRKFGESQIDYALGSAGRS
FVVGFGTNPPKRPHHRTAHSSWADSQSIPSYHRHTLYGALVGGPGSDDSYTDDISNYVNN
EVACDYNAGFVGALAKMYQLYGGNPIPDFKAIETPTNDEFFVEAGINASGTNFIEIKAIV
NNQSGWPARATDKLKFRYFVDLSELIKAGYSPNQLTLSTNYNQGAKVSGPYVWDASKNIY
YILVDFTGTLIYPGGQDKYKKEVQFRIAAPQNVQWDNSNDYSFQDIKGVSSGSVVKTKYI
PLYDGDVKVWGEEPGTSGATPTPTATATPTPTPTVTPTPTPTPTSTATPTPTPTPTVTPT
PTPTPTATPTATPTPTSTPSSTPVAGGQIKVLYANKETNSTTNTIRPWLKVVNTGSSSID
LSRVTIRYWYTVDGDKAQSAISDWAQIGASNVTFKFVKLSSSVSGADYYLEIGFKSGAGQ
LQAGKDTGEIQIRFNKSDWSNYNQGNDWSWMQSMTNYGENVKVTAYIDGVLVWGQEPSGA
TPTPTATPAPTVTPTPTPTPTSTPTATPTATPTPTPTPSSTPVAGGQIKVLYANKETNST
TNTIRPWLKVVNTGSSSIDLSRVTIRYWYTVDGDKAQSAISDWAQIGASNVTFKFVKLSS
SVSGADYYLEIGFKSGAGQLQAGKDTGEIQIRFNKSDWSNYNQGNDWSWMQSMTNYGENV
KVTAYIDGVLVWGQEPSGATPTPTATPAPTVTPTPTPAPTPTPTPTPTATPTPTPTPTPT
ATPTVTATPTPTPSSTPSVLGEYGQRFMWLWNKIHDPANGYFNQDGIPYHSVETLICEAP
DYGHLTTSEAFSYYVWLEAVYGKLTGDWSKFKTAWDTLEKYMIPSAEDQPMRSYDPNKPA
TYAGEWETPDKYPSPLEFNVPVGKDPLHNELVSTYGSTLMYGMHWLMDVDNWYGYGKRGD
GVSRASFINTFQRGPEESVWETVPHPSWEEFKWGGPNGFLDLFIKDQNYSKQWRYTDAPD
ADARAIQATYWAKVWAKEQGKFNEISSYVAKAAKMGDYLRYAMFDKYFKPLGCQDKNAAG
GTGYDSAHYLLSWYYAWGGALDGAWSWKIGSSHVHFGYQNPMAAWALANDSDMKPKSPNG
ASDWAKSLKRQIEFYRWLQSAEGAIAGGATNSWNGRYEKYPAGTATFYGMAYEPNPVYHD
PGSNTWFGFQAWSMQRVAEYYYVTGDKDAGALLEKWVSWVKSVVKLNSDGTFAIPSTLDW
SGQPDTWNGAYTGNSNLHVKVVDYGTDLGITASLANALLYYSAGTKKYGVFDEGAKNLAK
ELLDRMWKLYRDEKGLSAPEKRADYKRFFEQEVYIPAGWIGKMPNGDVIKSGVKFIDIRS
KYKQDPDWPKLEAAYKSGQAPEFRYHRFWAQCDIAIANATYEILFGNQ

ATGAACGTGAAAAAGTTCCCTGAAGGATTCCTCTGGGGTGTTGCAACAGCTTCCTACCAG
ATCGAGGGTTCTCCCCTCGCAGACGGAGCTGGTATGTCTATCTGGCACACCTTCTCCCAT
ACTCCTGGAAATGTAAAGAACGGTGACACGGGAGATGTGGCCTGCGACCACTACAACAGA
TGGAAAGAGGACATTGAAATCATAGAGAAACTCGGAGTAAAGGCTTACAGATTTTCAATC
AGCTGGCCAAGAATACTTCCGGAAGGAACAGGAAGGGTGAATCAGAAAGGACTGGATTTT
TACAACAGGATCATAGACACCCTGCTGGAAAAAGGTATCACACCCTTTGTGACCATCTAT
CACTGGGATCTTCCCTTCGCTCTTCAGCTGAAAGGAGGATGGGCGAACAGAGAAATAGCG
GATTGGTTCGCAGAATACTCAAGGGTTCTCTTTGAAAATTTCGGTGATCGTGTGAAGAAC
TGGATCACCTTGAACGAACCGTGGGTTGTTGCCATAGTGGGGCATCTGTACGGAGTCCAC
GCTCCTGGAATGAGAGATATTTACGTGGCTTTCCGAGCTGTTCACAATCTCTTGAGGGCA
CACGCCAGAGCGGTGAAAGTGTTCAGGGAAACCGTGAAAGATGGAAAGATCGGAATAGTT
TTCAACAATGGATATTTCGAACCTGCGAGTGAAAAAGAAGAAGACATCAGAGCGGTGAGA
TTCATGCATCAGTTCAACAACTATCCTCTCTTTCTCAATCCGATCTACAGAGGAGATTAC
CCGGAGCTCGTTCTGGAATTTGCCAGAGAGTATCTACCGGAGAATTACAAAGATGACATG
TCCGAGATACAGGAAAAGATCGACTTTGTTGGATTGAACTATTACTCCGGTCATTTGGTG
AAGTTCGATCCAGATGCACCAGCTAAGGTCTCTTTCGTTGAAAGGGATCTTCCAAAAACA
GCCATGGGATGGGAGATCGTTCCAGAAGGAATCTACTGGATCCTGAAGAAGGTGAAAGAA
GAATACAACCCACCAGAGGTTTACATCACAGAGAATGGGGCTGCTTTTGACGACGTAGTT
AGTGAAGATGGAAGAGTTCACGATCAAACAGAATCGATTATTTGAAGGCCCACATTGGT
CAGGCATGGAAGGCCATACAGGAGGGAGTGCCGCTTAAAGGTTACTTCGTCTGGTCGCTC
CTCGACAATTTCGAATGGGCAGAGGGATATTCCAAGAGATTTGGTATTGTGTATGTAGAC
TACAGCACTCAAAAACGCATCGTAAAACAGTGGGTACTGGTACTCGAATGTGGTTAAA
AACAACGGTCTGGAAGAC

B.

MNVKKFPEGFLWGVATASYQIEGSPLADGAGMSIWHTFSHTPGNVKNGDTGDVACDHYNRWKEDIEIIEK
LGVKAYRFSISWPRILPEGTGRVNQKGLDFYNRIIDTLLEKGITPFVTIYHWDLPFALQLKGGWANREIA
DWFAEYSRVLFENFGDRVKNWITLNEPWVVAIVGHLYGVHAPGMRDIYVAFRAVHNLLRAHARAVKVFRE
TVKDGKIGIVFNNGYFEPASEKEEDIRAVRFMHQFNNYPLFLNPIYRGDYPELVLEFAREYLPENYKDDM
SEIQEKIDFVGLNYYSGHLVKFDPDAPAKVSFVERDLPKTAMGWEIVPEGIYWILKKVKEEYNPPEVYIT
ENGAAFDDVVSEDGRVHDQNRIDYLKAHIGQAWKAIQEGVPLKGYFVWSLLDNFEWAEGYSKRFGIVYVD
YSTQKRIVKDSGYWYSNVVKNNGLED

```
GTGCCGCGCGCATTGCGGCGAGTGCCTGGCTCGCGGGTGATGCTGCGGGTCGGCGTCGTC
GTCGCGGTGCTGGCATTGGTTGCCGCACTCGCCAACCTAGCCGTGCCGCGGCCGGCTCGC
GCCGCGGGCGGCGGCTATTGGCACACGAGCGGCCGGGAGATCCTGGACGCGAACAACGTG
CCGGTACGGATCGCCGGCATCAACTGGTTTGGGTTCGAAACCTGCAATTACGTCGTGCAC
GGTCTCTGGTCACGCGACTACCGCAGCATGCTCGACCAGATAAAGTCGCTCGGCTACAAC
ACAATCCGGCTGCCGTACTCTGACGACATTCTCAAGCCGGGCACCATGCCGAACAGCATC
AATTTTTACCAGATGAATCAGGACCTGCAGGGTCTGACGTCCTTGCAGGTCATGGACAAA
ATCGTCGCGTACGCCGGTCAGATCGGCCTGCGCATCATTCTTGACCGCCACCGACCGGAT
TGCAGCGGGCAGTCGGCGCTGTGGTACACGAGCAGCGTCTCGGAGGCTACGTGGATTTCC
GACCTGCAAGCGCTGGCGCAGCGCTACAAGGGAAACCCGACGGTCGTCGGCTTTGACTTG
CACAACGAGCCGCATGACCCGGCCTGCTGGGGCTGCGGCGATCCGAGCATCGACTGGCGA
TTGGCCGCCGAGCGGGCCGGAAACGCCGTGCTCTCGGTGAATCCGAACCTGCTCATTTTC
GTCGAAGGTGTGCAGAGCTACAACGGAGACTCCTACTGGTGGGGCGGCAACCTGCAAGGA
GCCGGCCAGTACCCGGTCGTGCTGAACGTGCCGAACCGCCTGGTGTACTCGGCGCACGAC
TACGCGACGAGCGTCTACCCGCAGACGTGGTTCAGCGATCCGACCTTCCCCAACAACATG
CCCGGCATCTGGAACAAGAACTGGGGATACCTCTTCAATCAGAACATTGCACCGGTATGG
CTGGGCGAATTCGGTACGACACTGCAATCCACGACCGACCAGTGGCTGAAGACGCTC
GTCCAGTACCTACGGCCGACCGCGCAATACGGTGCGGACAGCTTCCAGTGGACCTTCTGG
TCCTGGAACCCCGATTCCGGCGACACAGGAGGAATTCTCAAGGATGACTGGCAGACGGTC
GACACAGTAAAAGACGGCTATCTCGCGCCGATCAAGTCGTCGATTTTCGATCCTGTCGGC
GCGTCTGCATCGCCTAGCAGTCAACCGTCCCCGTCGGTGTCGCCGTCTCCGTCGCCGAGC
CCGTCGGCGAGTCGGACGCCGACGCCTACTCCGACGCCGACAGCCAGCCCGACGCCAACG
CTGACCCCTACTGCTACGCCCACGCCCACGGCAAGCCCGACGCCGTCACCGACGGCAGCC
TCCGGAGCCCGCTGCACCGCGAGTTACCAGGTCAACAGCGATTGGGGCAATGGCTTCACG
GTAACGGTGGCCGTGACAAATTCCGGATCCGTCGCGACCAAGACATGGACGGTCAGTTGG
ACATTCGGCGGAAATCAGACGATTACCAATTCGTGGAATGCAGCGGTCACGCAGAACGGT
CAGTCGGTAACGGCTCGGAATATGAGTTATAACAACGTGATTCAGCCTGGTCAGAACACC
ACGTTCGGATTCCAGGCGAGCTATACCGGAAGCAACGCGGCACCGACAGTCGCCTGCGCA
GCAAGT
```

B.

```
MPRALRRVPGSRVMLRVGVVVAVLALVAALANLAVPRPARAAGGGYWHTSGREILDANNVPVRIAGINWF
GFETCNYVVHGLWSRDYRSMLDQIKSLGYNTIRLPYSDDILKPGTMPNSINFYQMNQDLQGLTSLQVMDK
IVAYAGQIGLRIILDRHRPDCSGQSALWYTSSVSEATWISDLQALAQRYKGNPTVVGFDLHNEPHDPACW
GCGDPSIDWRLAAERAGNAVLSVNPNLLIFVEGVQSYNGDSYWWGGNLQGAGQYPVVLNVPNRLVYSAHD
YATSVYPQTWFSDPTFPNNMPGIWNKNWGYLFNQNIAPVWLGEFGTTLQSTTDQTWLKTLVQYLRPTAQY
GADSFQWTFWSWNPDSGDTGGILKDDWQTVDTVKDGYLAPIKSSIFDPVGASASPSSQPSPSVSPSPSPS
PSASRTPTPTPTPTASPTPTLTPTATPTPTASPTPSPTAASGARCTASYQVNSDWGNGFTVTAVTNSGS
VATKTWTVSWTFGGNQTITNSWNAAVTQNGQSVTARNMSYNNVIQPGQNTTFGFQASYTGSNAAPTVACA
AS
```

Figure 5
A.
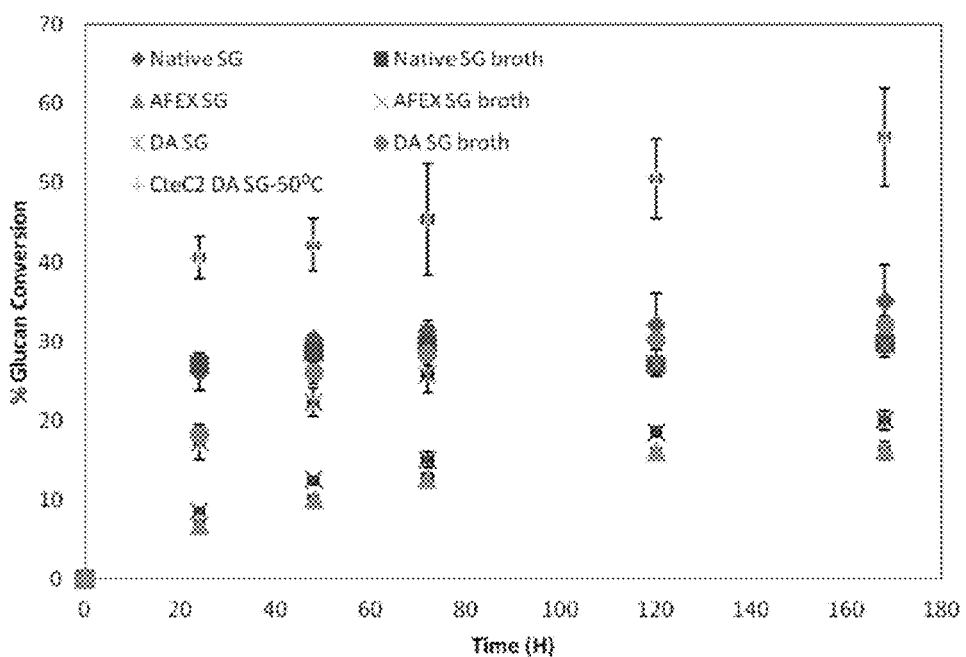
B.
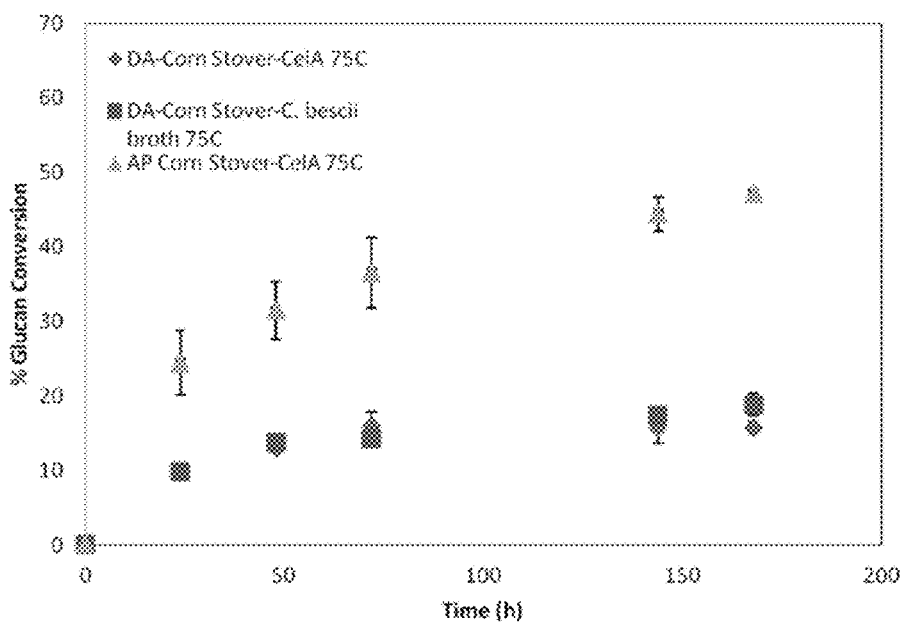

◆ CelA
■ Cel A + β-Gluc

◆ CelA
▲ Cel A + E1

◆ CelA
■ Cel A + β-Gluc + E1

◆ CelA
■ Cel A + β-Gluc + E1

ENZYMES FOR IMPROVED BIOMASS CONVERSION

CROSS-REFERENCE TO RELATED APPLICATIONS

This application claims priority to U.S. Provisional Application No. 61/671,208, filed Jul. 13, 2012, the contents of which are incorporated by reference in their entirety.

CONTRACTUAL ORIGIN

The United States Government has rights in this invention under Contract No. DE-AC36-08GO28308 between the United States Department of Energy and Alliance for Sustainable Energy, LLC, the Manager and Operator of the National Renewable Energy Laboratory.

REFERENCE TO SEQUENCE LISTING

This application contains a Sequence Listing submitted as an electronic text file entitled "12-28_ST25.txt," having a size in bytes of 64 kb and created on Jul. 12, 2013. Pursuant to 37 CFR §1.52(e)(5), the information contained in the above electronic file is hereby incorporated by reference in its entirety.

BACKGROUND

Lignocellulosic biomass is an abundant source of fermentable sugars, and biofuels derived from these renewable sources represent one of the best alternatives to petroleum-based fuels. Efficient conversion of lignocellulosic biomass, however, remains a challenge due to its inherent recalcitrance. Given the current state of technology of simultaneous saccharification and fermentation (SFF) and the commercial enzyme cocktails available, various chemical and thermal pretreatment steps are required to achieve meaningful conversation of biomass. Another alternative seen as viable and cost competitive for the future is consolidated bioprocessing (CBP), in which case saccharolytic enzyme are produced by the CBP organisms, which also ferment sugars released from biomass to the end product.

In nature, most cellulolytic organisms are of two types: those with non-complexed cellulases, xylanases, and hemicellulases produced by aerobic fungi and most bacteria; and those where cellulases, xylanases, and hemicellulases are complexed on a protein scaffold. This latter case is known only for a few anaerobic bacteria and fungi. In both cases, the enzymes secreted have a wide range of complexity but are mostly equipped with a single catalytic domain. An alternate enzymatic system, midway between the two previous paradigms, is one where the most abundant enzymes secreted are not only multi-modular but possess more than one catalytic domain. This strategy could present several advantages; it allows the synergistic effects between several catalytic domains usually found in cellulosomal systems but also lessen problems that cellulosomes may encounter due to their size.

The foregoing examples of the related art and limitations related therewith are intended to be illustrative and not exclusive. Other limitations of the related art will become apparent to those of skill in the art upon a reading of the specification and a study of the drawings.

SUMMARY

The following embodiments and aspects thereof are described and illustrated in conjunction with systems, tools and methods that are meant to be exemplary and illustrative, not limiting in scope. In various embodiments, one or more of the above-described problems have been reduced or eliminated, while other embodiments are directed to other improvements.

Exemplary embodiments provide methods for degrading cellulose or lignocellulosic biomass by contacting a cellulose containing material or lignocellulosic biomass with an enzyme cocktail comprising a thermostable enzyme comprising a GH9 domain and a GH48 domain and a thermostable β-glucosidase.

In certain embodiments, the thermostable enzyme comprising a GH9 domain and a GH48 domain is from a bacterium of the genus *Caldicellulosiruptor*, such as *Caldicellulosiruptor bescii* CelA.

In some embodiments, the thermostable β-glucosidase is from a bacterium of the genus *Thermotoga*, such as *Thermotoga maritima*.

In further embodiments, the enzyme cocktail further comprises a thermostable endoglucanase, which may be from a bacterium of the genus *Acidothermus*, such as *Acidothermus cellulolyticus*. One example is *Acidothermus cellulolyticus* E1.

Also provided are enzyme cocktails comprising *Caldicellulosiruptor bescii* CelA, a thermostable β-glucosidase, such as a β-glucosidase from the bacterium *Thermotoga maritima*, and a thermostable endoglucanase, such as *Acidothermus cellulolyticus* E1.

Further provided are methods for producing a biofuel from lignocellulosic biomass by contacting the lignocellulosic biomass with an enzyme cocktail described herein and converting the sugars to a biofuel by fermentation.

In addition to the exemplary aspects and embodiments described above, further aspects and embodiments will become apparent by reference to the drawings and by study of the following descriptions.

BRIEF DESCRIPTION OF THE DRAWINGS

Exemplary embodiments are illustrated in referenced figures of the drawings. It is intended that the embodiments and figures disclosed herein are to be considered illustrative rather than limiting.

FIG. 1 shows the nucleotide (A; SEQ ID NO:1) and amino acid (B; SEQ ID NO:2) sequences for CelA from *Caldicellulosiruptor bescii*. Locations of the GH9 and GH48 domains are indicated in bold and underline, respectively.

FIG. 2 shows the nucleotide (A; SEQ ID NO:3) and amino acid (B; SEQ ID NO:4) sequences for β-glucosidase from *Thermotoga maritima*.

FIG. 3 shows the nucleotide (A; SEQ ID NO:5) and amino acid (B; SEQ ID NO:6) sequences for E1 from *A. cellulolyticus*.

FIG. 5 shows the glucan conversion by CelA and *C. bescii* culture broth on switchgrass substrates (A) or corn stover substrates (B) subjected to various pretreatments.

DETAILED DESCRIPTION

Figure 4:
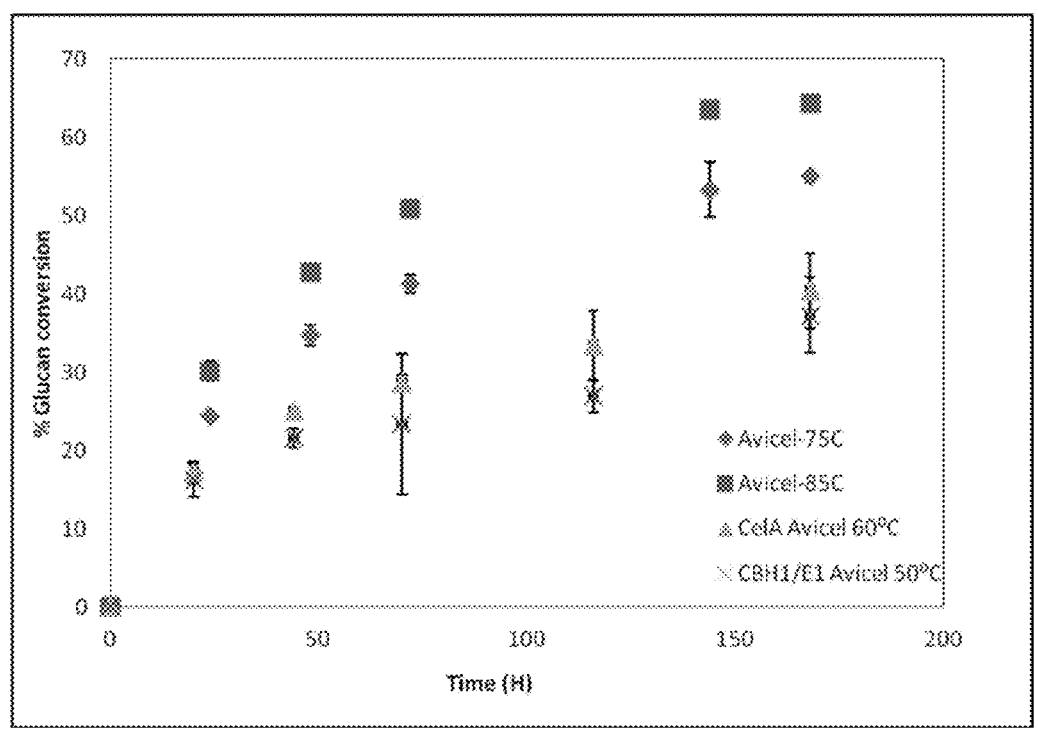
FIG. 4 shows the avicel conversion by CelA at three different temperatures compared to CBH1/E1 at the same loading (15 mg/g).

Disclosed herein are enzymes useful for the hydrolysis of cellulose and the conversion of biomass. While single enzymes disclosed herein digest cellulose and biomass, various combinations of the enzymes show synergistic activities on the substrates. Methods of degrading cellulose and biomass using enzymes and cocktails of enzymes are also disclosed.

Enzymatic conversion of biomass is currently performed using mixtures of mesophillic enzymes derived from fungi such as *T. reesei*. These mixtures utilize GH 6 and 7 cellulases to perform most of the cellulose hydrolysis work. An alternative approach is to utilize enzymes from hyperthermophillic bacterial organisms that contain no GH 7 enzymes for either simultaneous saccharification and fermentation (SSF) or single step direct microbial conversion of biomass. These hyperthermophillic systems utilize a combination of GH 9 and GH 48 enzymes to deconstruct cellulose and can operate at extremely high temperatures.

One such system is the cellulase system from *Caldicellulosiruptor bescii*, which includes the multidomain (GH 9/GH 48) enzyme CelA. As discussed in detail below, the addition of a thermostable beta glucosidase (β-glucosidase) (e.g., from *Thermotoga maritima*) and/or a thermostable endoglucanase (e.g., from *Acidothermus cellulolyticus*) to purified enzyme preparations of CelA or to *C. bescii* culture broths synergistically improves digestion of cellulose and biomass. The addition of these enzymes to an existing enzyme cocktail or a host organism used to produce an enzyme mixture may also significantly improve the performance of these enzyme mixtures, thus improving overall conversion yields, lowering the total enzyme concentrations required to reach a specified level of conversion or reducing the total time required to reach a specified level of conversion.

Without being bound by any particular theory, thermostable endoglucanases and beta-glucosidases may synergistically enhance the function of *C. bescii* cellulases such as CelA by increasing the number of reducing ends accessible to the CelA enzyme and relieving end product inhibition effects. As used herein, "thermostable" refers to enzymes that exhibit significant activity at elevated temperatures (e.g., over 70° C.) for several days.

Thermostable endoglucanases such as E1 from *A. cellulolyticus* combined with thermostable β-glucosidases such as those from *T. maritima* may synergistically improve the activity of GH 9/GH 48 enzymes such as CelA enzymes or cocktails containing CelA enzymes acting on biomass and the overall extent of conversion of biomass by the combined enzymes. The enhanced extent of glucan conversion exhibited by this enzyme combination indicates that there is synergy between the *A. cellulolyticus* E1 endoglucanase and *T. maritima* β-glucosidase with the *C. bescii* CelA enzyme, as well as the whole *C. bescii* culture broth.

The *Caldicellulosiruptor* species *C. bescii* presents several key features that make it an attractive candidate as a consolidated bioprocessing (CBP) microbe. For example, *C. bescii* grows well on crystalline cellulose as well as unpretreated substrates such as switchgrass and poplar at 75° C. Other species of the genus *Caldicellulosiruptor* include *C. obsidiansis, C. kronotskiensis, C. hydrothermalis, C. owensensis, C. saccharolyticus, C. lactoaceticus, C. acetigenus*, and *C. kristjanssonii*.

CelA is a complex enzyme containing an N-terminal GH9 endo-beta-1,4-glucanase, three family 3 carbohydrate binding modules (CBMIII), and a C-terminal GH48 exo-beta-1, 4-glucanase. CelA is capable of withstanding temperatures over 90° C. and has an optimal activity at the 85-90° C. range making it a good candidate for an industrial process where higher temperatures are desired and where costly steps after pretreatment can be avoided. CelA also combines the strengths of a chain-end forming endoglucanase and an efficient cellobiohydrolase on the same protein. This combination allows CelA to be efficient on highly crystalline cellulose substrates. Also, it outperforms one of the most efficient fungal combinations of Exo/Endo-glucanases on avicel even at the temperature of 60° C., far from ideal for CelA. Finally, CelA exhibits hydrolytic activity on xylan—an attractive feature from a process standpoint where biomass feedstocks used are rich in xylan.

β-glucosidases are a family of exocellulase enzymes that catalyze the cleavage of β(1-4) linkages in substrates such as cellobiose, resulting in the release of glucose. The β-glucosidase from *T. maritima* (whose sequence is set forth in FIG. 2) is provided as a specific example, but other β-glucosidases may be suitable for use in the enzyme cocktails and methods described herein.

Suitable thermostable β-glucosidases include those derived from bacteria of the genus *Thermotoga*, including the species *T. maritima*. Other species of the genus *Thermotoga* include *T. elfii, T. hypogeal, T. lettingae, T. naphthophila, T. neapolitana, T. petrophila, T. subterranean*, and *T. thermarum*.

Endoglucanases suitable for use in the cocktails and methods include thermostable endoglucanases from organisms of the genus *Acidothermus*, including *A. cellulolyticus*, and the E1 endoglucanase from *A. cellulolyticus* (the sequence of which is presented in FIG. 3).

The components of enzyme cocktails may be varied depending on the nature of the substrate being degraded and the pretreatment protocol applied to the substrate. Exemplary enzyme cocktails may comprise, by weight, 30-95% of a thermostable GH 9/GH 48 enzyme such as CelA, 5-25% of a thermostable β-glucosidase, 5-40% of a thermostable endoglucanase such as E1, and 1-20% of additional enzymes such as xylanases (e.g., the thermostable XynA from *A. cellulolyticus*) or β-xylosidases. Accessory enzymes may also be included at relatively small percentages of the enzyme cocktail. A thermostable GH 9/GH 48 enzyme such as CelA may be comprise at least about 30%, 35%, 40%, 45%, 50%, 55%, 60%, 65%, 70%, 75%, 80%, 85%, 90%, or 95% of the enzyme cocktail. A thermostable β-glucosidase may comprise at least about 5%, 10%, 15%, 20%, or 25% of the enzyme cocktail. A thermostable endoglucanase such as E1 may comprise at least about 5%, 10%, 15%, 20%, 25%, 30%, 35% or 40% of the enzyme cocktail. A thermostable xylanase or β-xylosidase may comprise at least about 1%, 2%, 3%, 4%, 5%, 6%, 7%, 8%, 9%, 10%, 11%, 12%, 13%, 14%, 15%, 16%, 17%, 18%, 19% or 20% of the enzyme cocktail. Additional accessory enzymes may comprise at least about 1%, 2%, 3%, 4%, 5%, 6%, 7%, 8%, 9% or 10% of the enzyme cocktail.

The enzyme cocktails exhibit surprisingly improved cellulase activities when compared to the individual enzyme activities or the additive effect of each enzyme. The term "improved activity" refers to an increased rate of conversion of a cellulosic substrate or a specific component thereof. Relative activities can be determined using conventional assays, including those discussed in the Examples below. Additional assays suitable for determining cellulase activity include hydrolysis assays on industrially relevant cellulose-containing substrates such as pretreated corn stover. Hydrolysis assays on crystalline cellulose or amorphous cellulose or on small molecule fluorescent reporters may also be used to determine cellulase activity. In certain embodiments, cellulase activity is expressed as the amount of time or enzyme concentration needed to reach a certain percentage (e.g., 80%) of cellulose conversion to sugars.

Enzymes described herein may be used as purified recombinant enzyme or as culture broths from cells that naturally produce the enzyme or that have been engineered to produce the enzyme. In certain embodiments, enzyme cocktails may achieve cellulose conversions to sugars (as a percentage of the total cellulose in the original substrate) ranging from 50% to 100%, 70% to 100%, or 90% to 100%. In some embodiments, the cellulose conversion exhibited by the enzyme cocktail may be at least about 50%, 55%, 60%, 65%, 70%, 75%, 80%, 85%, 90%, 95%, or 99%.

Methods for degrading cellulose and materials containing cellulose using the enzymes and enzyme cocktails are also provided herein. For example, the enzyme cocktails may be used in compositions to help degrade (e.g., by liquefaction) a variety of cellulose products (e.g., paper, cotton, etc.) in landfills. The enzyme cocktails may also be used to enhance the cleaning ability of detergents, function as a softening agent or improve the feel of cotton fabrics (e.g., stone washing or biopolishing) or in feed compositions.

Cellulose containing materials may also be degraded to sugars using the enzymes. Ethanol may be subsequently produced from the fermentation of sugars derived from the cellulosic materials. Exemplary cellulose-containing materials include bioenergy crops, agricultural residues, municipal solid waste, industrial solid waste, sludge from paper manufacture, yard waste, wood and forestry waste. Examples of biomass include, but are not limited to, corn grain, corn cobs, crop residues such as corn husks, corn stover, corn fiber, grasses, wheat, wheat straw, barley, barley straw, hay, rice straw, switchgrass, waste paper, sugar cane bagasse, sorghum, soy, components obtained from milling of grains, trees, branches, roots, leaves, wood (e.g., poplar) chips, sawdust, shrubs and bushes, vegetables, fruits, flowers and animal manure.

Biofuels such as ethanol may be produced by saccharification and fermentation of lignocellulosic biomass such as trees, herbaceous plants, municipal solid waste and agricultural and forestry residues. Typically, saccharification is carried out by contacting the lignocellulosic biomass with an enzyme cocktail that includes one or more of the enzymes described herein. Such enzyme cocktails may also contain one or more endoglucanases (such as the Family 5 endoglucanase E1 from *Acidothermus cellulolyticus*) or one or more β-glucosidases (e.g., a β-glucosidase from *A. niger*) to optimize hydrolysis of the lignocelluloses. Additional suitable endoglucanases include EGI, EGII, EGIII, EGIV, EGV or Cel7B (e.g., Cel7B from *T. reesei*). Enzyme cocktails may also include accessory enzymes such as hemicellulases, pectinases, oxidative enzymes, and the like.

Enzymes with the ability to degrade carbohydrate-containing materials, such as cellulases with endoglucanase activity, exoglucanase activity, or β-glucosidase activity, or hemicellulases with endoxylanase activity, exoxylanase activity, or β-xylosidase activity may be included in enzyme cocktails. Examples include enzymes that possess cellobiohydrolase, α-glucosidase, xylanase, β-xylosidase, α-galactosidase, β-galactosidase, α-amylase, glucoamylases, arabinofuranosidase, mannanase, β-mannosidase, pectinase, acetyl xylan esterase, acetyl mannan esterase, ferulic acid esterase, coumaric acid esterase, pectin methyl esterase, laminarinase, xyloglucanase, galactanase, glucoamylase, pectate lyase, chitinase, exo-β-D-glucosaminidase, cellobiose dehydrogenase, ligninase, amylase, glucuronidase, ferulic acid esterase, pectin methyl esterase, arabinase, lipase, glucosidase or glucomannanase activities.

A lignocellulosic biomass or other cellulosic feedstock may be subjected to pretreatment at an elevated temperature in the presence of a dilute acid, concentrated acid or dilute alkali solution for a time sufficient to at least partially hydrolyze the hemicellulose components before adding the enzyme cocktail. Additional suitable pretreatment regimens include ammonia fiber expansion (AFEX), treatment with hot water or steam, or lime pretreatment. A lignocellulosic biomass or other cellulosic feedstock may also be de-acetylated before or after the pretreatment regimens listed above.

Lignocellulosic biomass and other cellulose containing materials are contacted with enzymes at a concentration and a temperature for a time sufficient to achieve the desired amount of cellulose degradation. The enzymes and cocktails disclosed herein may be used at any temperature, but are well suited for higher temperature digestions. For example, the enzymes or cocktails may be used at temperatures ranging from about 50° C. to about 60° C., from about 60° C. to about 70° C., from about 70° C. to about 80° C., from about 80° C. to about 90° C., from about 90° C. to about 100° C., from about 50° C. to about 100° C., from about 60° C. to about 90° C., from about 70° C. to about 85° C., or from about 80° C. to about 85° C. Exemplary temperatures include 60, 61, 62, 63, 64, 65, 66, 67, 68, 69, 70, 71, 72, 73, 74, 75, 76, 77, 78, 79, 80, 81, 82, 83, 84, 85, 86, 87, 88, 89 and 90° C.

Suitable times for cellulose degradation range from a few hours to several days, and may be selected to achieve a desired amount of degradation. Exemplary digestion times include 1, 2, 3, 4, 5, 6, 7, 8, 9, 10, 11, or 12 hours; and 0.5, 1, 1.5, 2, 2.5, 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5 or 15 days. In some embodiments, digestion times may be one or more weeks.

A reducing agent may also be added to the digestion mixture to improve the cellulose degradation by the enzyme mixture. Exemplary reducing agents include cysteine and dithiothreitol. Reducing agents may be added at concentrations ranging from 1 nM to 100 mM (e.g., 1 mM).

Separate saccharification and fermentation is a process whereby cellulose present in biomass is converted to glucose that is subsequently converted to ethanol by yeast or bacteria strains. Simultaneous saccharification and fermentation is a process whereby cellulose present in biomass is converted to glucose and, at the same time and in the same reactor, converted into ethanol by yeast or bacteria strains. Enzyme cocktails may be added to the biomass prior to or at the same time as the addition of a fermentative organism.

The resulting products after cellulose degradation may also be converted to products other than ethanol. Examples include conversion to higher alcohols, hydrocarbons, or other advanced fuels via biological or chemical pathways, or combination thereof.

"Nucleic acid" or "polynucleotide" as used herein refers to purine- and pyrimidine-containing polymers of any length, either polyribonucleotides or polydeoxyribonucleotide or mixed polyribo-polydeoxyribonucleotides. This includes single- and double-stranded molecules (i.e., DNA-DNA, DNA-RNA and RNA-RNA hybrids) as well as "protein nucleic acids" (PNA) formed by conjugating bases to an amino acid backbone. This also includes nucleic acids containing modified bases.

Nucleic acids referred to herein as "isolated" are nucleic acids that have been removed from their natural milieu or separated away from the nucleic acids of the genomic DNA or cellular RNA of their source of origin (e.g., as it exists in cells or in a mixture of nucleic acids such as a library), and may have undergone further processing. Isolated nucleic acids include nucleic acids obtained by methods described herein, similar methods or other suitable methods, including essentially pure nucleic acids, nucleic acids produced by chemical synthesis, by combinations of biological and chemical methods, and recombinant nucleic acids that are isolated.

Nucleic acids referred to herein as "recombinant" are nucleic acids which have been produced by recombinant DNA methodology, including those nucleic acids that are generated by procedures that rely upon a method of artificial replication, such as the polymerase chain reaction (PCR) and/or cloning into a vector using restriction enzymes. Recombinant nucleic acids also include those that result from recombination events that occur through the natural mechanisms of cells, but are selected for after the introduction to the cells of nucleic acids designed to allow or make probable a desired recombination event. Portions of isolated nucleic acids that code for polypeptides having a certain function can be identified and isolated by, for example, the method disclosed in U.S. Pat. No. 4,952,501.

An isolated nucleic acid molecule can be isolated from its natural source or produced using recombinant DNA technology (e.g., polymerase chain reaction (PCR) amplification, cloning) or chemical synthesis. Isolated nucleic acid molecules can include, for example, genes, natural allelic variants of genes, coding regions or portions thereof, and coding and/or regulatory regions modified by nucleotide insertions, deletions, substitutions, and/or inversions in a manner such that the modifications do not substantially interfere with the nucleic acid molecule's ability to encode a polypeptide or to form stable hybrids under stringent conditions with natural gene isolates. An isolated nucleic acid molecule can include degeneracies. As used herein, nucleotide degeneracy refers to the phenomenon that one amino acid can be encoded by different nucleotide codons. Thus, the nucleic acid sequence of a nucleic acid molecule that encodes a protein or polypeptide can vary due to degeneracies.

Unless so specified, a nucleic acid molecule is not required to encode a protein having protein activity. A nucleic acid molecule can encode a truncated, mutated or inactive protein, for example. In addition, nucleic acid molecules may also be useful as probes and primers for the identification, isolation and/or purification of other nucleic acid molecules, independent of a protein-encoding function.

Suitable nucleic acids include fragments or variants that encode a functional enzyme. For example, a fragment can comprise the minimum nucleotides required to encode a functional cellulase. Nucleic acid variants include nucleic acids with one or more nucleotide additions, deletions, substitutions, including transitions and transversions, insertion, or modifications (e.g., via RNA or DNA analogs). Alterations may occur at the 5' or 3' terminal positions of the reference nucleotide sequence or anywhere between those terminal positions, interspersed either individually among the nucleotides in the reference sequence or in one or more contiguous groups within the reference sequence.

In certain embodiments, a nucleic acid may be identical to the sequences represented in FIGS. 1-3. In other embodiments, the nucleic acids may be least about 80%, 81%, 82%, 83%, 84%, 85%, 86%, 87%, 88%, 89%, 90%, 91%, 92%, 93%, 94%, 95%, 96%, 97%, 98% or 99% identical to the sequences represented in FIG. 1-3, or 80%, 81%, 82%, 83%, 84%, 85%, 86%, 87%, 88%, 89%, 90%, 91%, 92%, 93%, 94%, 95%, 96%, 97%, 98% or 99% identical to the sequences represented in FIGS. 1-3. Sequence identity calculations can be performed using computer programs, hybridization methods, or calculations. Exemplary computer program methods to determine identity and similarity between two sequences include, but are not limited to, the GCG program package, BLASTN, BLASTX, TBLASTX, and FASTA. The BLAST programs are publicly available from NCBI and other sources. For example, nucleotide sequence identity can be determined by comparing query sequences to sequences in publicly available sequence databases (NCBI) using the BLASTN2 algorithm.

Embodiments of the nucleic acids include those that encode the polypeptides that functions as cellulases or functional equivalents thereof. The amino acid sequences of exemplary enzymes are depicted in FIGS. 1-3. A functional equivalent includes fragments or variants of these that exhibit the ability to function as a cellulase. As a result of the degeneracy of the genetic code, many nucleic acid sequences can encode a polypeptide having, for example, the amino acid sequence Shown in FIGS. 1-3. Such functionally equivalent variants are contemplated herein.

Altered or variant nucleic acids can be produced by one of skill in the art using the sequence data illustrated herein and standard techniques known in the art. Variant nucleic acids may be detected and isolated by hybridization under high stringency conditions or moderate stringency conditions, for example, which are chosen to prevent hybridization of nucleic acids having non-complementary sequences. "Stringency conditions" for hybridizations is a term of art that refers to the conditions of temperature and buffer concentration that permit hybridization of a particular nucleic acid to another nucleic acid in which the first nucleic acid may be perfectly complementary to the second, or the first and second may share some degree of complementarity that is less than perfect.

Nucleic acids may be derived from a variety of sources including DNA, cDNA, synthetic DNA, synthetic RNA, or combinations thereof. Such sequences may comprise genomic DNA, which may or may not include naturally occurring introns. Moreover, such genomic DNA may be obtained in association with promoter regions or poly (A) sequences. The sequences, genomic DNA, or cDNA may be obtained in any of several ways. Genomic DNA can be extracted and purified from suitable cells by means well known in the art. Alternatively, mRNA can be isolated from a cell and used to produce cDNA by reverse transcription or other means.

Also disclosed herein are recombinant vectors, including expression vectors, containing nucleic acids encoding enzymes. A "recombinant vector" is a nucleic acid molecule that is used as a tool for manipulating a nucleic acid sequence of choice or for introducing such a nucleic acid sequence into a host cell. A recombinant vector may be suitable for use in cloning, sequencing, or otherwise manipulating the nucleic acid sequence of choice, such as by expressing or delivering the nucleic acid sequence of choice into a host cell to form a recombinant cell. Such a vector typically contains heterologous nucleic acid sequences not naturally found adjacent to a nucleic acid sequence of choice, although the vector can also contain regulatory nucleic acid sequences (e.g., promoters, untranslated regions) that are naturally found adjacent to the nucleic acid sequences of choice or that are useful for expression of the nucleic acid molecules.

The nucleic acids described herein may be used in methods for production of enzymes and enzyme cocktails through incorporation into cells, tissues, or organisms. In some embodiments, a nucleic acid may be incorporated into a vector for expression in suitable host cells. The vector may then be introduced into one or more host cells by any method known in the art. One method to produce an encoded protein includes transforming a host cell with one or more recombinant nucleic acids (such as expression vectors) to form a recombinant cell. The term "transformation" is generally used herein to refer to any method by which an exogenous nucleic acid molecule (i.e., a recombinant nucleic acid molecule) can be inserted into a cell, but can be used interchangeably with the term "transfection."

Non-limiting examples of suitable host cells include cells from microorganisms such as bacteria, yeast, fungi, and filamentous fungi. Exemplary microorganisms include, but are not limited to, bacteria such as strains of *Bacillus brevis, Bacillus megaterium, Bacillus subtilis, Caulobacter crescentus,* and *Escherichia coli* (e.g., BL21 and K12); filamentous fungi from the genera *Trichoderma* (e.g., *T. reesei, T. viride, T. koningii,* or *T. harzianum*), *Penicillium* (e.g., *P. funiculosum*), *Humicola* (e.g., *H. insolens*), *Chrysosporium* (e.g., *C. lucknowense*), *Gliocladium, Aspergillus* (e.g., *A. niger, A. nidulans, A. awamori,* or *A. aculeatus*), *Fusarium, Neurospora, Hypocrea* (e.g., *H. jecorina*), and *Emericella*; and yeasts from the genera *Saccharomyces* (e.g., *S. cerevisiae*), *Pichia* (e.g., *P. pastoris*), or *Kluyveromyces* (e.g., *K. lactis*). Cells from plants such as Arabidopsis, barley, citrus, cotton, maize, poplar, rice, soybean, sugarcane, wheat, switch grass, alfalfa, miscanthus, and trees such as hardwoods and softwoods are also contemplated herein as host cells.

Host cells can be transformed, transfected, or infected as appropriate by any suitable method including electroporation, calcium chloride-, lithium chloride-, lithium acetate/polyene glycol-, calcium phosphate-, DEAE-dextran-, liposome-mediated DNA uptake, spheroplasting, injection, microinjection, microprojectile bombardment, phage infection, viral infection, or other established methods. Alternatively, vectors containing the nucleic acids of interest can be transcribed in vitro, and the resulting RNA introduced into the host cell by well-known methods, for example, by injection. Exemplary embodiments include a host cell or population of cells expressing one or more nucleic acid molecules or expression vectors described herein (for example, a genetically modified microorganism). The cells into which nucleic acids have been introduced as described above also include the progeny of such cells.

Vectors may be introduced into host cells such as those from filamentous fungi by direct transformation, in which DNA is mixed with the cells and taken up without any additional manipulation, by conjugation, electroporation, or other means known in the art. Expression vectors may be expressed by filamentous fungi or other host cells episomally or the gene of interest may be inserted into the chromosome of the host cell to produce cells that stably express the gene with or without the need for selective pressure. For example, expression cassettes may be targeted to neutral chromosomal sites by recombination.

Host cells carrying an expression vector (i.e., transformants or clones) may be selected using markers depending on the mode of the vector construction. The marker may be on the same or a different DNA molecule. In prokaryotic hosts, the transformant may be selected, for example, by resistance to ampicillin, tetracycline or other antibiotics. Production of a particular product based on temperature sensitivity may also serve as an appropriate marker.

Host cells may be cultured in an appropriate fermentation medium. An appropriate, or effective, fermentation medium refers to any medium in which a host cell, including a genetically modified microorganism, when cultured, is capable of growing or expressing the polypeptides described herein. Such a medium is typically an aqueous medium comprising assimilable carbon, nitrogen and phosphate sources, but can also include appropriate salts, minerals, metals and other nutrients. Microorganisms and other cells can be cultured in conventional fermentation bioreactors and by any fermentation process, including batch, fed-batch, cell recycle, and continuous fermentation. The pH of the fermentation medium is regulated to a pH suitable for growth of the particular organism. Culture media and conditions for various host cells are known in the art. A wide range of media for culturing filamentous fungi, for example, are available from ATCC. Exemplary culture/fermentation conditions and reagents are provided in the Examples that follow.

The nucleic acid molecules described herein encode the enzymes with amino acid sequences such as those represented by FIGS. 1-3. As used herein, the terms "protein" and "polypeptide" are synonymous. "Peptides" are defined as fragments or portions of polypeptides, preferably fragments or portions having at least one functional activity as the complete polypeptide sequence. "Isolated" proteins or polypeptides are proteins or polypeptides purified to a state beyond that in which they exist in cells. In certain embodiments, they may be at least 10% pure; in others, they may be substantially purified to 80% or 90% purity or greater. Isolated proteins or polypeptides include essentially pure proteins or polypeptides, proteins or polypeptides produced by chemical synthesis or by combinations of biological and chemical methods, and recombinant proteins or polypeptides that are isolated. Proteins or polypeptides referred to herein as "recombinant" are proteins or polypeptides produced by the expression of recombinant nucleic acids.

Proteins or polypeptides encoded by nucleic acids as well as functional portions or variants thereof are also described herein. Polypeptide sequences may be identical to the amino acid sequences presented in FIGS. 1-3, or may include up to a certain integer number of amino acid alterations. Such protein or polypeptide variants retain functionality as cellulases, and include mutants differing by the addition, deletion or substitution of one or more amino acid residues, or modified polypeptides and mutants comprising one or more modified residues. The variant may have one or more conservative changes, wherein a substituted amino acid has similar structural or chemical properties (e.g., replacement of leucine with isoleucine). Alterations may occur at the amino- or carboxy-terminal positions of the reference polypeptide sequence or anywhere between those terminal positions, interspersed either individually among the amino acids in the reference sequence or in one or more contiguous groups within the reference sequence.

In certain embodiments, the polypeptides may be at least about 80%, 81%, 82%, 83%, 84%, 85%, 86%, 87%, 88%, 89%, 90%, 91%, 92%, 93%, 94%, 95%, 96%, 97%, 98% or 99% identical to the amino acid sequences set forth in FIGS. 1-3 and possess enzymatic function. Percent sequence identity can be calculated using computer programs (such as the BLASTP and TBLASTN programs publicly available from NCBI and other sources) or direct sequence comparison. Polypeptide variants can be produced using techniques known in the art including direct modifications to isolated polypeptides, direct synthesis, or modifications to the nucleic acid sequence encoding the polypeptide using, for example, recombinant DNA techniques.

Polypeptides may be retrieved, obtained, or used in "substantially pure" form, a purity that allows for the effective use of the protein in any method described herein or known in the art. For a protein to be most useful in any of the methods described herein or in any method utilizing enzymes of the types described herein, it is most often substantially free of contaminants, other proteins and/or chemicals that might interfere or that would interfere with its use in the method (e.g., that might interfere with enzyme activity), or that at least would be undesirable for inclusion with a protein.

EXAMPLES

Example 1

Bacterial Strains and Growth Conditions

*C. bescii* DSM 6725 cells were grown at 75° C. under anaerobic conditions on Avicel. Non-avicel bound proteins were pre-affinity purified on a phenyl sepharose column.

Example 2

Purification of CelA

The CelA holoenzyme was initially purified with anion exchange chromatography using a Source 15Q column (GE Healthcare, Piscataway, N.J.). For this chromatography, buffer A was 20 mM Tris, pH 6.8 and buffer B was 20 mM Tris, pH 6.8, with 1 M NaCl. The resulting fraction was then further purified using a source 15PHE hydrophobic interaction column (GE Healthcare, Piscataway, N.J.), with buffer A and buffer C, 20 mM acetate, pH 5.0, with 1 M ammonium sulfate. Relevant fractions were then subjected to size exclusion chromatography using a Sephacryl 300 column (GE Healthcare, Piscataway, N.J.) and eluted with buffer D, 20 mM acetate, pH 5.0, and 100 mM NaCl. The relevant CelA containing fractions were further purified with anion exchange chromatography using a Source 15Q column (GE Healthcare, Piscataway, N.J.) and buffer F, 20 mM Tris-HCL, pH 8.0, and buffer G, 20 mM Tris-HCL, pH 8.0, with 1 M NaCl. The relevant CelA containing fractions were further purified with hydrophobic interaction chromatography using a Source 15ISO column (GE Healthcare, Piscataway, N.J.) with buffer A (20 mM Tris-HCL, pH 8.0) and buffer B (20 mM Tris-HCL, pH 8.0 with 1 M ammonium sulfate. The CelA-containing fractions were once again subjected to size exclusion chromatography using a Sephacryl 300 column (GE Healthcare, Piscataway, N.J.) and eluted with buffer D, 20 mM acetate, pH 5.0 and 100 mM NaCl. The purified fusion proteins were concentrated with a Vivaspin 10K concentrator (Vivaproducts, Littleton, Mass.), and the protein concentration was determined with a Pierce BCA protein assay (Pierce, Rockford, Ill.).

Example 3

Expression of CelA GH48 and GH9 Modules

CelA CBM3-GH48 construct was overexpressed with N-terminal his-tag in *E. coli*. It was amplified by primers ACACCGGCTAGCAGCAGCACACCTGTAGCAGG (SEQ ID NO:7) and TAGCTTCTCGAGTTATTGATTGCCAA-ACAGTA (SEQ ID NO:8) (the restriction sites are underlined), and the template of the genomic DNA of *C. bescii* was employed. The PCR fragment was inserted into the plasmid of pET28b (Novagen, Madison, Wis.), and was overexpressed in the *E. coli* BL21(DE3) strain (Stratagene, La Jolla, Calif.) at 37° C. with addition of 0.3 mM isopropyl-β-D-thiogalactopyranoside (IPTG).

The GH9 construct from CelA was overexpressed with N-terminal his-tag in *E. coli*. It was amplified by primers of ATGCTAGCTAGCGGTTCGTTTAACTATGGGGA (SEQ ID NO:9) and GTCGTTCTCGAGTCATTCAATAGC-TTTGAAATCTG (SEQ ID NO:10) (the restriction sites are underlined), and the template of the genomic DNA of *C. bescii* was employed. The PCR fragment was inserted into the plasmid of pET28b (Novagen, Madison, Wis.), and was overexpressed in the *E. coli* BL21(DE3) strain (Stratagene, La Jolla, Calif.) at 37° C. with addition of 0.3 mM isopropyl-β-D-thiogalactopyranoside (IPTG).

Example 4

Purification of CelA GH48 and GH9 Modules

The CelA GH48 component was first desalted into 20 mM acetic acid, pH 5.5, and then ammonium sulfate was added to a concentration of 2 M. This fraction was subjected to hydrophobic interaction chromatography using a Source 15PHE column (GE Healthcare, Piscataway, N.J.). For this chromatography, buffer A was 20 mM acetic acid, pH 5.5, and with 2 M ammonium sulphate, buffer B was 20 mM acetic acid, pH 5.5. The resulting peak was then purified using a source 15Q anion interaction column (GE Healthcare, Piscataway, N.J.), with buffer A (20 mM Tris, pH 6.8) and buffer C (20 mM Tris, pH 6.8, with 1 M NaCl. Finally, CelA-GH48 was separated from minor impurities by size exclusion chromatography using HiLoad Superdex 75 (26/60) (GE Healthcare, Piscataway, N.J.) in buffer H (20 mM acetate, pH 5.0, with 100 mM NaCl). The purified protein was concentrated with a Vivaspin 5K concentrator (Vivaproducts, Littleton, Mass.), and the concentration determined using the Pierce BCA assay (Pierce, Rockford, Ill.).

The *C. bescii* GH9 module was further purified by first dialyzing it twice against 1.5 L of buffer A (20 mM acetic acid, pH 5.5, 1 mM EDTA with 1 mM DTT) followed by cation exchange chromatography using a Source 15S column (GE Healthcare, Piscataway, N.J.). For this chromatography, buffer A and buffer B with additional 1 M NaCl were used. Finally, minor impurities were removed by size exclusion chromatography using HiLoad Superdex 75 (26/60) (GE Healthcare, Piscataway, N.J.) in 20 mM Tris-HCl, pH 7.0, containing 100 mM NaCl, 5 mM $CaCl_2$, 1 mM EDTA, and 1 mM sodium azide. The purified protein solution was concentrated with a Vivaspin 5K concentrator (Vivaproducts, Littleton, Mass.), and its concentration was measured using a NanoDrop UV spectrophotometer (NanoDrop, Wilmington, Del.).

Example 5

Substrates and Biomass Samples

Avicel (ph101), corn stover, and switchgrass samples were used to evaluate the cellulolytic efficiency of CelA, raw *C. bescii* broth, and enzyme cocktails. The biomass samples were submitted to several types of pretreatments with increasing severity including diluted acid and ammonia fiber explosion (AFEX) pretreatments for both corn stover and switchgrass; and alkaline peroxide pretreatment for corn stover. The details of each pretreatment condition are described in Table 1.

g glucan. Digestion assays using fungal enzymes were performed at 50° C. and an enzyme concentration of 12 mg/g of Cbh1 from *T. reesei* and 3 mg/g of E1 from *A. cellulolyticus*. Both bacterial and fungal digestion assays were done in 20 mM acetate, pH 5.5, containing 10 mM $CaCl_2$, and 100 mM NaCl with continuous mixing.

Digestions were run continuously for seven days and sugar release was monitored. Samples were taken at various time points, enzymes were inactivated by boiling for 15 minutes and samples were then filtered through 0.45 um Acrodisc syringe filters and analyzed for Glucose, Xylose, and Cellobiose by HPLC. Samples were injected at 20 μL and run on an Agilent 1100 HPLC system equipped with a BioRad Aminex HPX-87H 300 mm×7.8 mm column heated to 55° C. A constant flow of 0.6 mL/min was used with 0.1 M $H_2SO_4$ in water as the mobile phase to give separation of the analytes. Glucose, xylose, and cellobiose were quantified against independent standard curves. All experiments were performed in triplicate and the resulting extents of conversion are shown as percent glucan converted.

Additionally, CelA and its two recombinant catalytic domains, GH48 and GH9, were tested for activity on 5 mM para-nitrophenol-β-D-xylopyranoside (PnP-X) and para-nitrophenol-β-D-cellobioside (PnP-C) in 20 mM acetate buffer,

TABLE 1

| Pretreatement conditions | | | | Compositional analysis (%) | | | | | | | |
|---|---|---|---|---|---|---|---|---|---|---|---|
| | Catalyst | Temp (° C.) | Time (min) | Glucan | Xylan | Galactan | Arabinan | Mannan | Lignin | Ash | Protein |
| Dilute acid pretreated corn stover | % 0.5 $_4SO_2H$ | 150 | 20 | 39.73 | 21.18 | 1.33 | 3 | ND | 24.3 | 7.06 | 1.56 |
| Alkaline peroxide pretreated corn stover | % 2.5 $_2O_2H$ | 65 | 60 | 59 | 28 | 0 | 1.9 | 0 | 6.2 | 1 | ND |
| Native Switchgrass | NA | NA | NA | 30.2 | 21.3 | ND | 3.1 | 5.3 | 17.4 | 6.4 | 2.3 |
| Dilute Acid Pretreated Switchgrass | % 5 $_4SO_2H$ | 190 | 1 | 42.59 | 5.48 | 0.47 | 0.3 | 0 | 21.52 | 6.09 | ND |
| AFEX pretreated Switchgrass | g/g 1.52 biomass | 150 | 30 | 30.2 | 21.3 | ND | 3.1 | 5.3 | 17.4 | 6.4 | 2.3 |
| Avicel ph101 | NA | NA | NA | 94.94 | 1.48 | 0.12 | 0.31 | ND | 0.54 | 0.1 | ND |
| De-acetylated, dilute acid pretreated corn stover | | | | 63.91 | 5.01 | 0.63 | 0.82 | | 23.93 | 4.07 | |

To provide a basis for the maximum theoretical sugar yield achievable from each substrate during enzymatic hydrolysis, portions of each of the pretreated solids samples were dried and subjected to the standard two-stage sulfuric acid hydrolysis method for determining structural carbohydrates in lignocelluloses as described by Sluiter and coworkers (NREL Technical Report: NREL/TP-510-42623 (2006)). In this method, the carbohydrate content of each pretreated sample is calculated from the carbohydrates released.

Example 6

Enzyme Activity Assays

Enzyme activities were determined at 60° C., 75° C., and 85° C. at an enzyme concentration of 15 or 20 mg protein per pH 5.5, 50 mM NaCl at 75° C. The incubation was performed for one hour and then quenched with 50 μl of 1 M calcium carbonate. Absorbance was read at 405 nm.

Example 7

Crystallization

Screening for crystals was done with sitting drop vapor diffusion using a 96-well plate and Crystal Screen HT, PEG ion HT and Grid Screen Salt HT from Hampton Research (Aliso Viejo, Calif.). 50 μL of well solution with drops containing 1 μL of well solution and 1 μL of protein solution were used for screening and a 24-well hanging drop vapor diffusion setup with 1 ml of well solution and drops containing 1 μL of well solution and 1 μL of protein solution was used for optimization of crystallization conditions. The GH9 protein solution contained 9.5 mg/mL of protein, 20 mM Tris pH 7, 100 mM NaCl, 5 mM $CaCl_2$, 1 mM EDTA and 1 mM Na azide. The best crystals for the unliganded GH9 formed in 0.1 M Na cacodylate pH 6.4, 1.8 M ammonium sulfate and 10% dioxane using a 24 well optimization plate. Before flash freezing, the crystal was soaked in a 2 µL cryo solution drop with 10% (v/v) ethylene glycol and 10% (v/v) glycerol in the well solution and incubated for 5 seconds. The crystals of GH9 with cellobiose were obtained using other crystals from the same condition with an excess amount of cellobiose powder in the cryo solution drop and by incubating for 30 seconds. The GH48 protein solution contained 1.8 mg/mL of protein in 20 mM acetic acid pH 5, with 100 mM NaCl. Crystals were grown in 0.1 M tri-sodium citrate, pH 5.8, 20% (w/v) PEG 4000 and 20% (v/v) 2-propanol using a 24 well optimization plate. Before flash freezing, the crystal was incubated for 5 seconds in a 2 µL cryo solution drop containing 10% (v/v) ethylene glycol and 10% (v/v) glycerol in the well solution.

Example 8

X-Ray Diffraction, Structure Determination, and Structure Analysis

Before data collection, all crystals were flash-frozen in a cold nitrogen gas stream at 100 K. Data collection was performed using a Bruker X8 MicroStar X-Ray generator with Helios mirrors and Bruker Platinum 135 CCD detector. Data was indexed and processed with the Bruker Suite of programs version 2008.1-0 (Bruker AXS, Madison, Wis.). Intensities were converted into structure factors and 5% of the reflections were flagged for Rfree calculations using programs F2MTZ, Truncate, CAD and Unique from the CCP4 package of programs. The GH9 structures were solved using molecular replacement program Molrep with PDB entry 1KSD as a model. The GH48 structure was solved using MrBump with PDB entry 1G9G as a model. For all three structures, ARP/wARP version 7.0 and Coot version 0.6.2 was used for multiple cycles of automatic and manual model building. Further refinement and manual correction was performed using REFMACS version 5.6.0117 and Coot. The resulting structures have been deposited to the Protein Data Bank with PDB codes 4DOD (GH9), 4DOE (GH9-CB) and 4EL8 (GH48).

Programs Coot, PyMOL and ICM (molsoft) were used for comparing and analyzing structures. Ramachandran plot statistics were calculated using Molprobity and root mean square deviations (rmsd) of bond lengths and angles were calculated from ideal values of Engh and Huber stereochemical parameters. Wilson B-factor was calculated using CTRUNCATE version 1.0.11. Structural similarity searches were done using pair wise secondary structure matching by PDBefold.

Example 9

Enzymatic Activity on Model Substrates

The cellulolytic performance of purified CelA, isolated from the *C. bescii* enzyme broth, was examined at 60° C., 75° C., and 85° C. To remove any variability in the enzymatic digestion of biomass substrates such as differences in glucan content or pretreatments, the first enzymatic assays were performed with the model cellulose avicel PH-101. The percentage of glucan released over a seven-day digestion is shown in FIG. 4. CelA exhibited the most activity at the highest temperature tested, 85° C. This single enzyme can convert more than 60% of mostly crystalline cellulose content in 6 days. While lower temperatures impair the performance of CelA, losing close to 10-15% of its activity for every 10-degree temperature drop, its activity remains higher than most single cellulases tested in these conditions. Surprisingly, even at temperature of 60° C. where CelA has lost over 40% of its peak activity, it still outperforms a mixture of the fungal Cel7A from *T. reesei* (Cbh1) and E1 from *A. cellulolyticus*. At the same mg/g protein loading, CelA alone is about 2 times as effective compared to a current model mixture of enzymes with the same Exo-endo activity. However, on a molar basis (since CelA is about 4 times larger in terms of molecular weight), there is about ¼ less CelA enzyme present, making CelA about 8 times as active as the Cbh1/E1 combination.

Figure 7:
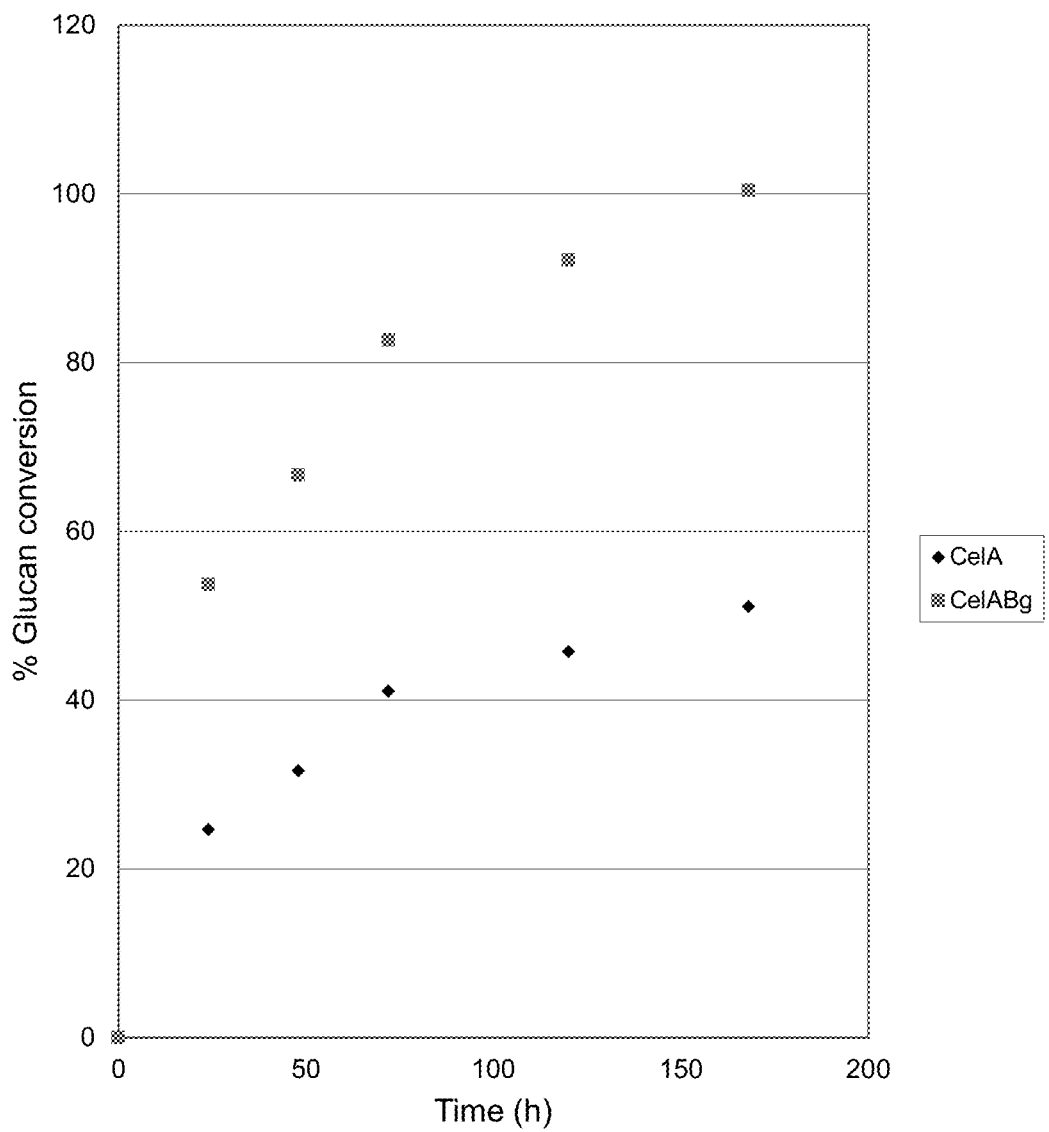
FIG. 7 shows a comparison of avicel conversion by CelA alone or in combination with β-glucosidase. Loadings were 15 mg/g CelA and 14 mg/g CelA 1 mg/g+β-glucosidase, respectively.
Figure 9:
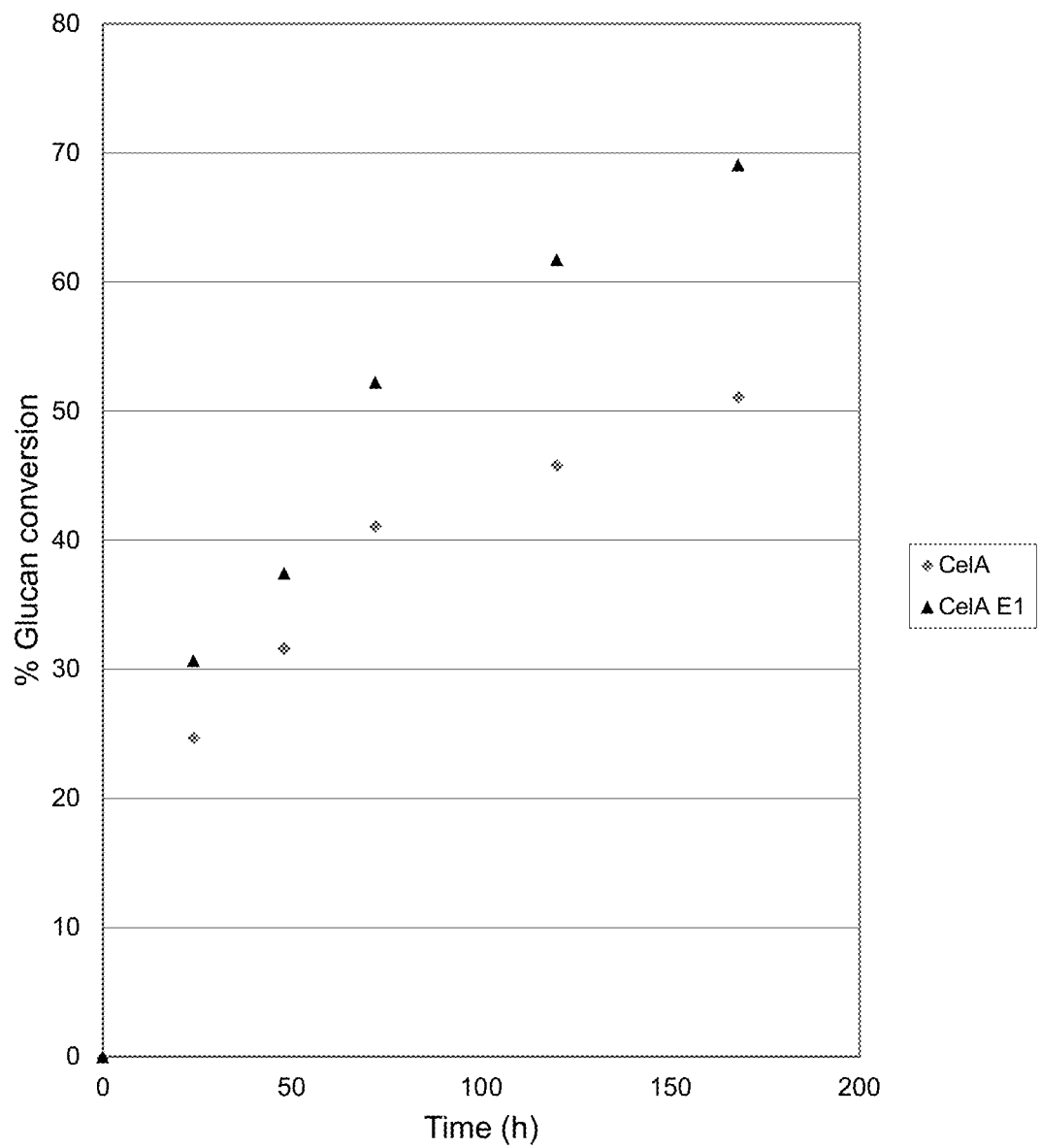
FIG. 9 shows a comparison of avicel conversion by CelA alone or in combination with E1. Loadings were 15 mg/g CelA and 11 mg/g CelA 4 mg/g+E1, respectively.
Figure 11:
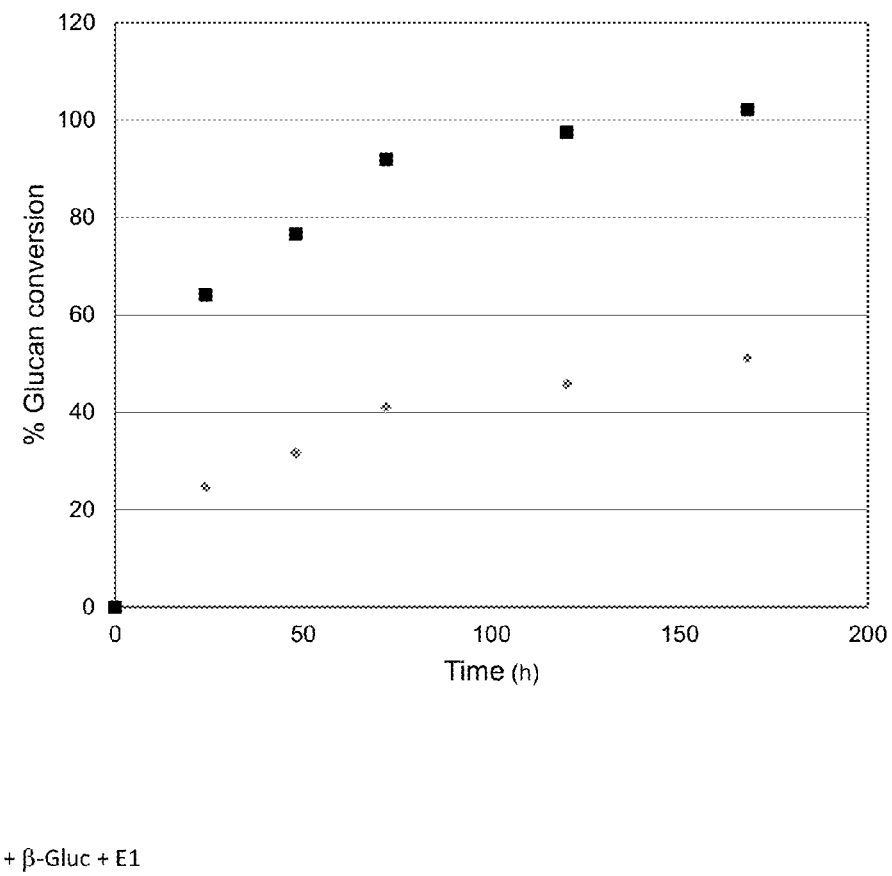
FIG. 11 shows a comparison of avicel conversion by CelA alone or in combination with β-glucosidase and E1. Loadings were 15 mg/g CelA and 10 mg/g CelA 1 mg/g+β-glucosidase+4 mg/g E1, respectively.

The cellulolytic performance of purified CelA, alone or in combination with E1 from *A. cellulolyticus* and/or β-glucosidase from *T. maritima*, on avicel at 75° C. was also tested. Total enzyme loadings were 15 mg protein per g glucan. As shown in FIGS. 7, 9 and 11, the addition of small amounts of β-glucosidase (1 mg per g; FIG. 7) or E1 (4 mg per g; FIG. 9) or both (FIG. 11) to CelA surprisingly enhanced the enzymatic activity of the CelA in a synergistic manner.

Example 10

Enzymatic Activity on Untreated and Pretreated Biomass

The cellulolytic activity of CelA, *C. bescii* enzyme broth, and enzyme cocktails were tested on native switchgrass samples as well as some with varying pretreatment severity, including dilute acid (DA) and AFEX pretreatments. These enzymatic assays were performed at 75° C. and at a total protein loading of 15 mg of enzyme per g of feedstock. Under these conditions, the maximum glucan conversion of CelA peaks at 30-35% (FIG. 5A) on native switchgrass and dilute acid pretreated switchgrass. CelA activity was the lowest for AFEX pretreated switchgrass were the glucan conversion is 20%. Surprisingly, the activity of CelA on biomass is similar to that of the *C. bescii* enzyme broth. For comparison with CelA, the commercial enzyme preparation CTec2 was used on DA pretreated switchgrass at its optimal temperature of 50° C. The exact enzyme composition of CTec2 is unknown as it is proprietary; however, the mixture likely contains cellulases, hemicellulases, and beta-glucosidases from modified fungi. CTec2 achieves 63% conversion of glucans after 168 hours and outperforms CelA and *C. bescii* broth at the same enzyme loading of 15 mg/g.

Similarly, the enzymatic activity of CelA was also tested on a dilute acid (DA) and alkaline peroxide (AP) pretreated corn stover at 75° C. but an enzyme loading of 20 mg of enzyme per g of feedstock (FIG. 5B). CelA performs better on AP corn stover, with a conversion of close to 50%. The same result is observed for the *C. bescii* enzyme broth.

Figure 6:
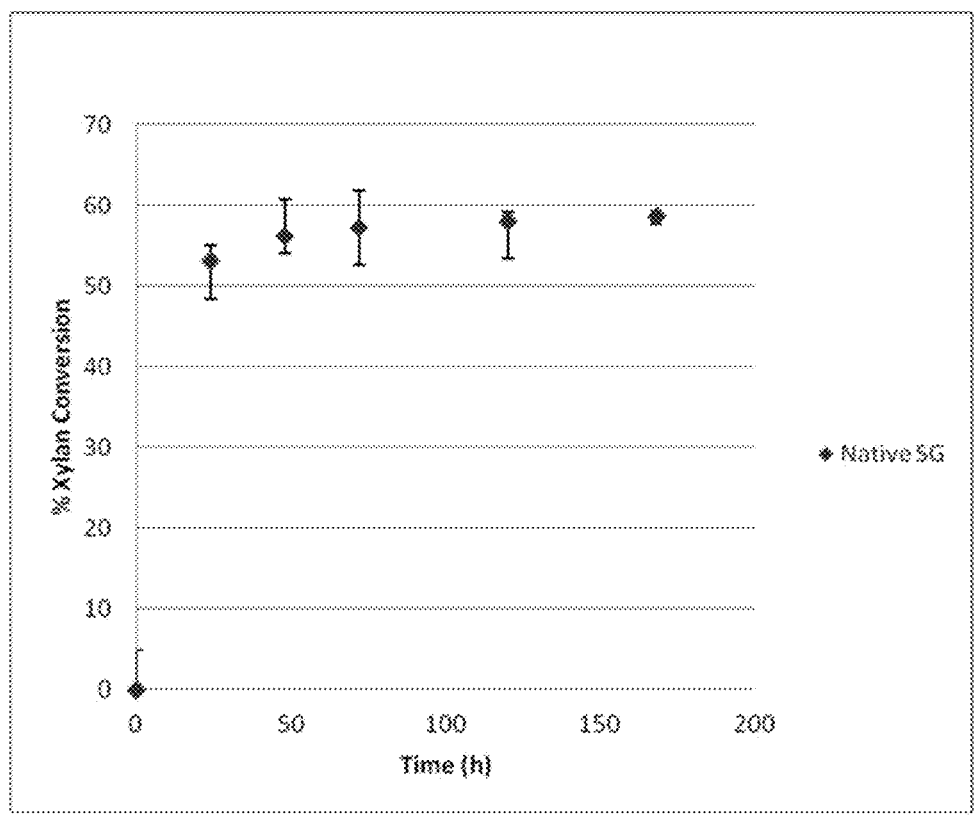
FIG. 6 shows the conversion of xylan present in native switchgrass by CelA.

The ability of CelA to convert xylan found in native switchgrass at 75° C. was also examined. As shown in FIG. 6, CelA can efficiently convert xylan when it is present in untreated biomass. Levels of xylan conversion approached 60% in these assays, which is much higher than expected.

Figure 8:
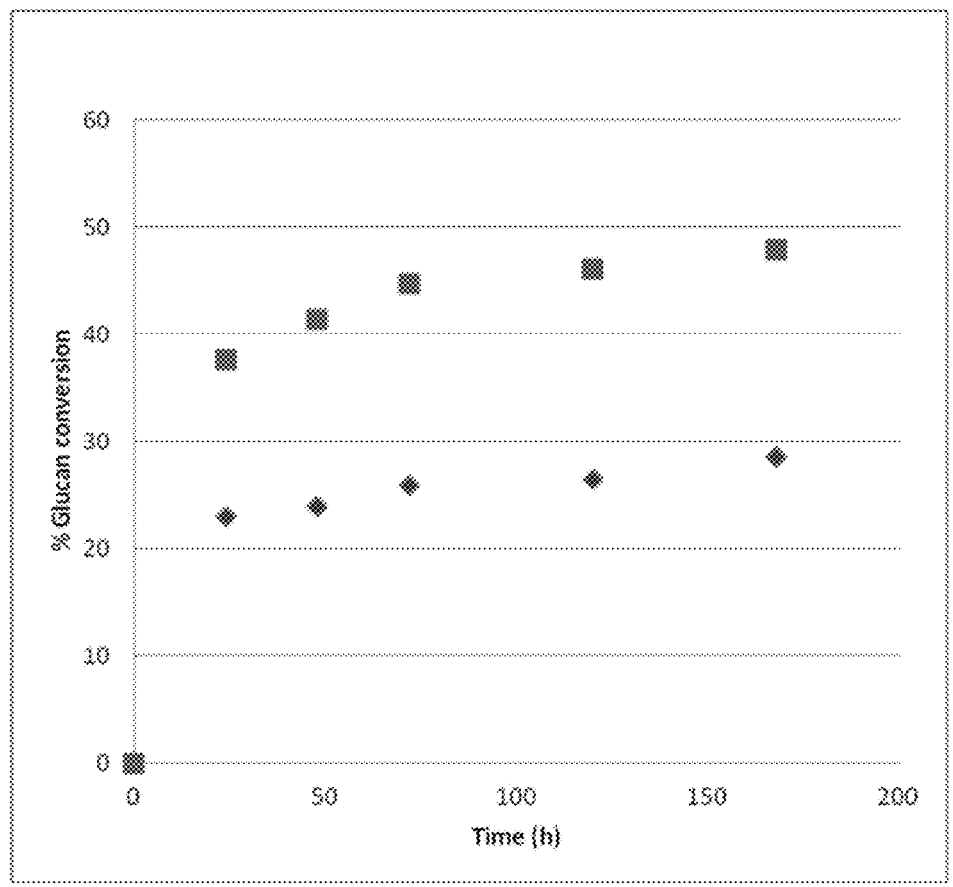
FIG. 8 shows a comparison of dilute acid pretreated corn stover conversion by CelA alone or in combination with β-glucosidase. Loadings were 15 mg/g CelA and 14 mg/g CelA+1 mg/g β-glucosidase, respectively.
Figure 10:
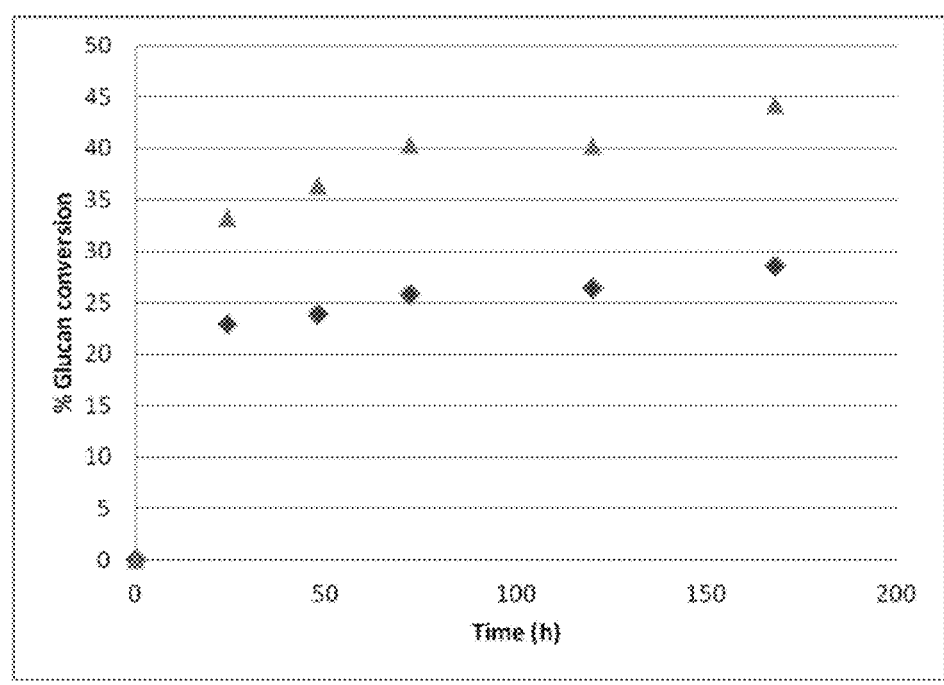
FIG. 10 shows a comparison of dilute acid pretreated corn stover conversion by CelA alone or in combination with E1. Loadings were 15 mg/g CelA and 11 mg/g CelA 4 mg/g+E1, respectively.
Figure 12:
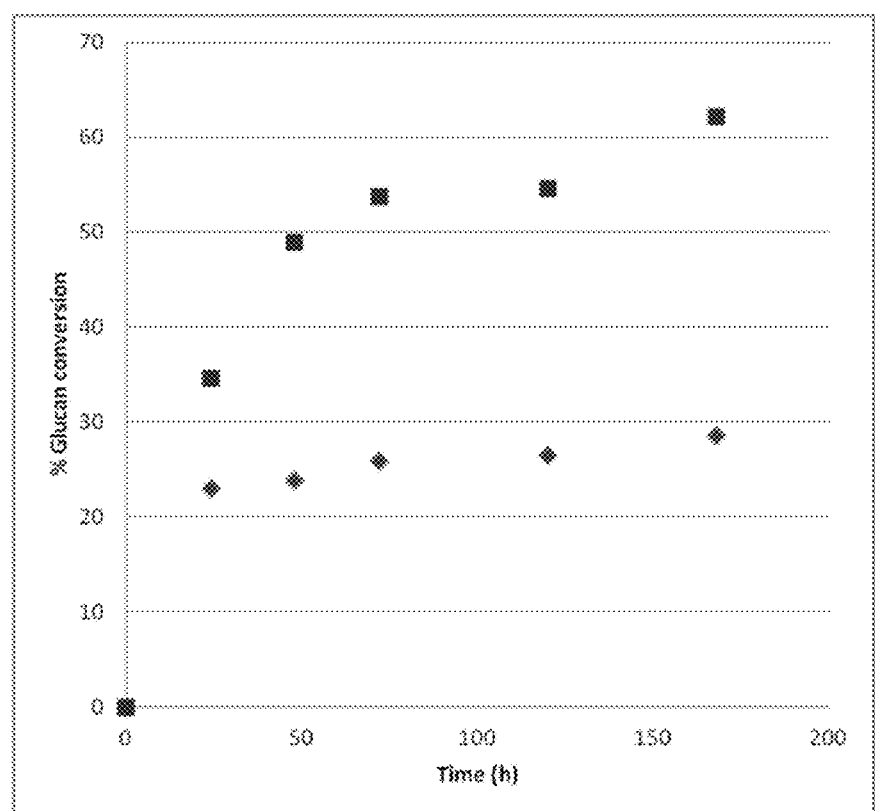
FIG. 12 shows a comparison of dilute acid pretreated corn stover conversion by CelA alone or in combination with β-glucosidase and E1. Loadings were 15 mg/g CelA and 10 mg/g CelA 1 mg/g+β-glucosidase+4 mg/g E1, respectively.

The enzymatic activity of purified CelA, alone or in combination with E1 from *A. cellulolyticus* and/or β-glucosidase from *T. maritima*, on DA pretreated corn stover at 75° C. was also tested. Total enzyme loadings were 15 mg protein per g glucan. As with activities seen on avicel, the addition of small amounts of β-glucosidase (1 mg per g; FIG. 8) or E1 (4 mg per g; FIG. 10) or both (FIG. 12) to CelA surprisingly enhanced the enzymatic activity of the CelA in a synergistic manner.

Example 11

Activity of CelA and CelA Components on PnP

The xylanase activity of CelA and its two catalytic units GH48 and GH9 was examined on para-nitrophenol-β-D-xylopyranoside (PnP-X) and para-nitrophenol-β-D-cellobioside (PnP-C). The results shown in Table 2 indicate that CelA and the GH48 module have activity on both substrates whereas the GH9 component has activity on cellulose. CelA was also able to achieve 60% conversion of xylan from native switchgrass, which shows its potential for an industrial process using mild to no pretreatment.

TABLE 2

|  | PnP-X | PnP-C |
| --- | --- | --- |
| CelA holoenzyme | +++ | ++++ |
| CelA GH48 | ++++ | ++++ |
| CelA GH9 | − | + |

Example 12

Crystal Structures of the *C. bescii* CelA GH9 and GH48 Modules

The structure of the unliganded *C. bescii* CelA GH9 module was refined to a resolution of 1.7 Å with R and Rfree of 0.155 and 0.179, respectively, and one molecule in the asymmetric unit. The GH9 module with cellobiose was refined to a resolution of 1.56 Å with R and Rfree of 0.148 and 0.175, respectively, and one molecule in the asymmetric unit. GH48 had a resolution of 2.45 Å with R and Rfree of 0.195 and 0.258 with one molecule in the asymmetric unit.

The GH9 module of CelA has an (alpha/alpha)6 barrel fold. The unliganded GH9 structure has one calcium atom, one 1,4-dioxane molecule, 11 ethylene glycol molecules, ten glycerol molecules and four sulfates. The liganded GH9 module has one cellobiose molecule and one cellotriose molecule bound at the active site and one calcium atom, one 1,4-dioxane molecule, 26 ethylene glycol molecules, six glycerol molecules and three sulfates bound elsewhere in the structure.

The GH48 module has an (alpha/alpha)6 barrel fold. The structure revealed one calcium atom, one ethylene glycol and one sulfate. The GH48 structure did not contain the CBM3 module that was included before it in the construct. The CBM3 module may have been cut from the GH48 because of degradation during the crystallization trials. The CelF (PDB entry 1FCE) numbering was used, starting from residue seven (of CelF) that was the first one visible in the electron density. The last three residues and a loop formed by residues 308 to 310 were not modeled due to weak or no electron density. The 308 to 310 loop was special because it actually had some density where the corresponding residues from CelF (PDB entry 1FCE) and CelS (PDB entry 1L1Y) are but the resulting model would be too inaccurate due to possible other overlapping conformations making the density weak and noisy leading to wrong conformations after refinement.

Pairwise secondary-structure matching of structures with at least 70% secondary structure similarity by PDBefold found 19 unique structural matches for the GH9 module (liganded structure was used) and 21 matches for GH48. Structures similar to CelA GH9 included other GH9s and glucuronyl hydrolases with varying sequence identities with a GH9 from *Clostridium thermocellum* (PDB entry 2XFG) being most similar (71% sequence identity). CelA GH48 was only similar to the different structures of CelF and CelS GH48.

Example 13

Enzymatic Activity, Time of Addition and Reducing Agents

Figure 13:
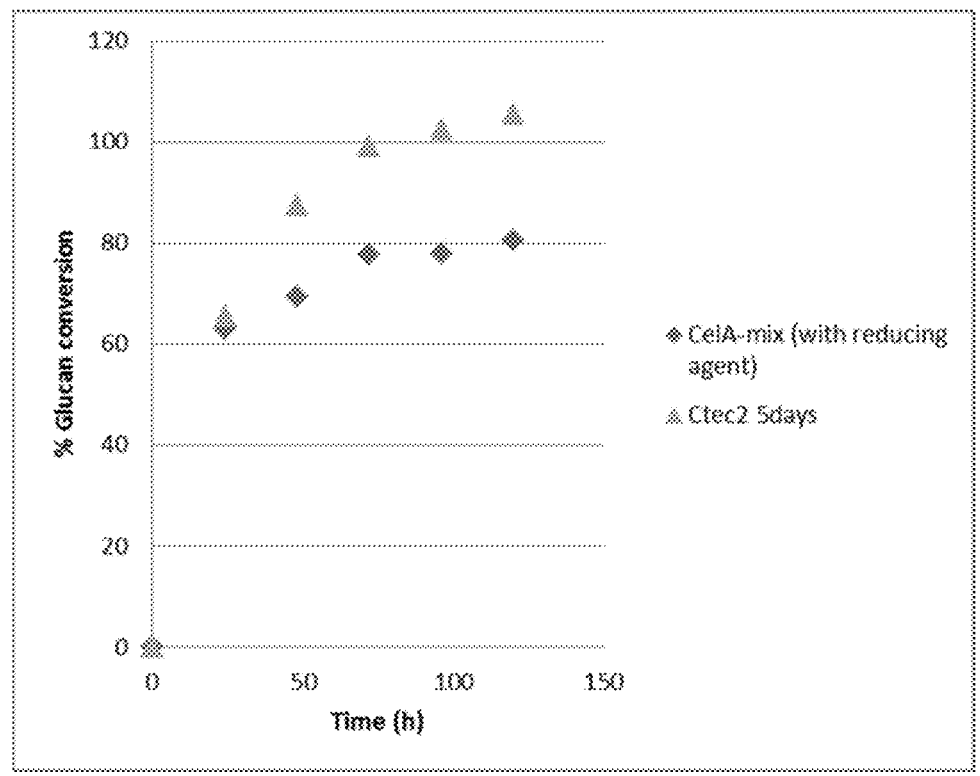
FIG. 13 shows a comparison of de-acetylated, dilute acid pretreated corn stover conversion by a CelA mixture (17 mg/g CelA; 2 mg/g E1; 1 mg/g *T. maratima* β-glucosidase) or a commercial enzyme preparation (Ctec2).

The cellulolytic activities of enzyme cocktails (17 mg/g CelA; 2 mg/g E1; 1 mg/g *T. maratima* β-glucosidase) were tested on samples of de-acetylated, dilute acid pretreated corn stover in a horizontal screw reactor. Results shown in FIG. 13 demonstrate that up to 80% conversion of this substrate can be achieved using the enzyme cocktails.

Figure 14:
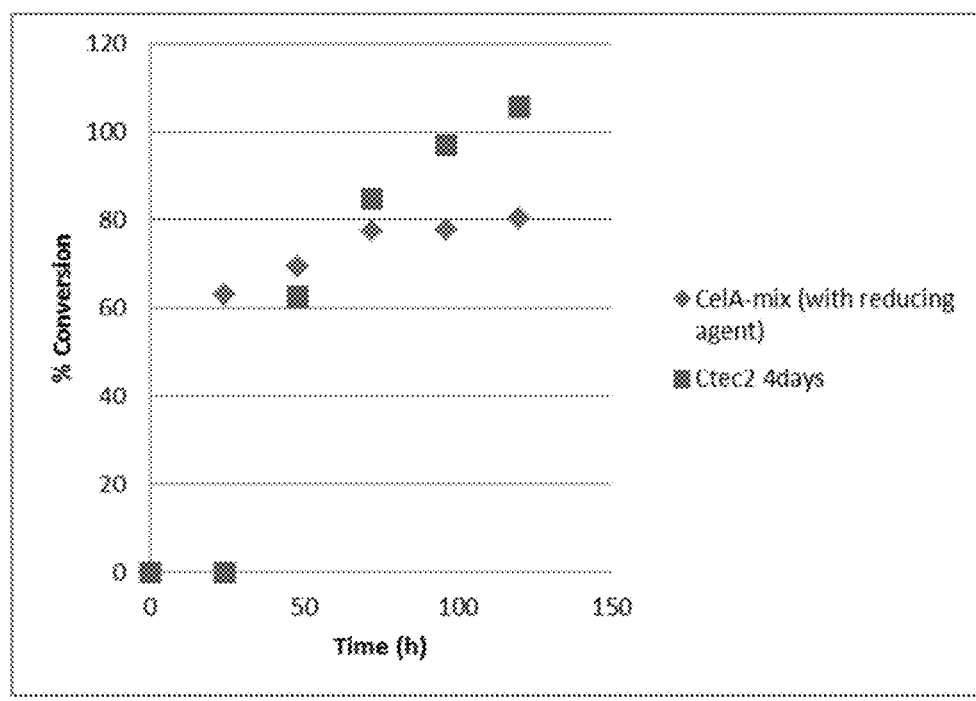
FIG. 14 shows a comparison of de-acetylated, dilute acid pretreated corn stover conversion by a CelA mixture (17 mg/g CelA; 2 mg/g E1; 1 mg/g *T. maratima* β-glucosidase) or a commercial enzyme preparation (Ctec2).

CelA enzyme cocktails may also be added to a reactor at a higher temperature than commercial enzyme preparations. Because large reactors take time and water/energy to cool, CelA mixtures can create savings in time and energy by being added earlier in the process (e.g., at 80° C. rather than cooling to 50° C.) without loss of enzymatic activity. FIG. 14 shows the activity of CelA mixture in comparison to a commercial enzyme cocktail.

Figure 15:
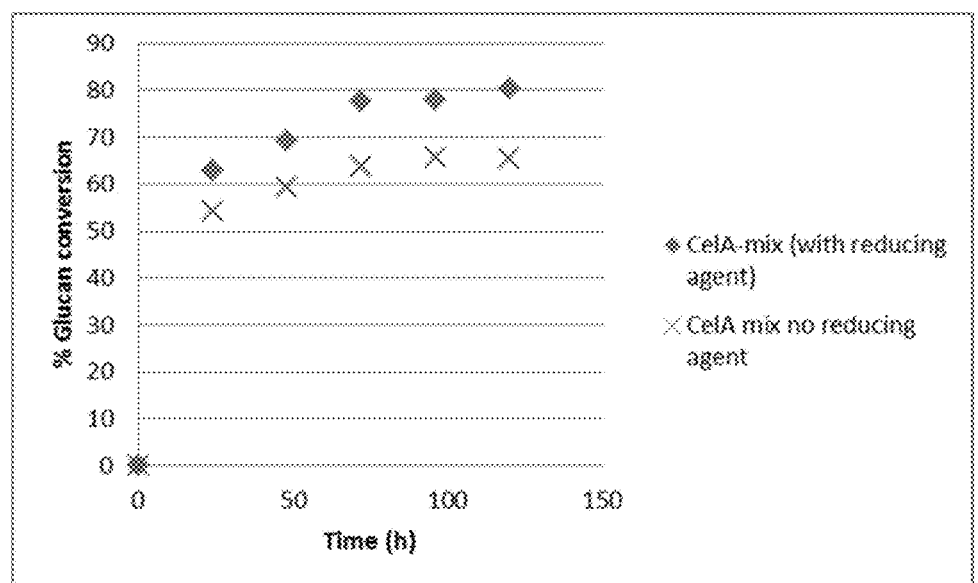
FIG. 15 shows a comparison of de-acetylated, dilute acid pretreated corn stover conversion by a CelA mixture (17 mg/g CelA; 2 mg/g E1; 1 mg/g *T. maratima* β-glucosidase) with or without a reducing agent (1 mM cysteine).

FIG. 15 shows the increase in overall conversion when a reducing agent is added to the reaction mixture. The addition of 1 mM cysteine improved the conversion by up to 20%.

The Examples discussed above are provided for purposes of illustration and are not intended to be limiting. Still other embodiments and modifications are also contemplated.

While a number of exemplary aspects and embodiments have been discussed above, those of skill in the art will recognize certain modifications, permutations, additions and sub combinations thereof. It is therefore intended that the following appended claims and claims hereafter introduced are interpreted to include all such modifications, permutations, additions and sub-combinations as are within their true spirit and scope.

We claim:

1. A method for degrading cellulose, comprising contacting a cellulose containing material with an enzyme cocktail comprising a recombinant thermostable enzyme from *Caldicellulosiruptor bescii* comprising a glycoside hydrolase (GH9) domain and a glycoside hydrolase (GH48) domain and a recombinant thermostable β-glucosidase, wherein at least 50% of the cellulose in the material is converted to at least one sugar.

2. The method of claim 1, wherein the thermostable enzyme comprising a GH9 domain and a GH48 domain is *Caldicellulosiruptor bescii* CelA.

3. The method of claim 1, wherein the thermostable β-glucosidase is from a bacterium of the genus *Thermotoga*.

4. The method of claim 1, wherein the enzyme cocktail further comprises a thermostable endoglucanase.

5. The method of claim 4, wherein the thermostable endoglucanase is from a bacterium of the genus *Acidothermus*.

6. The method of claim 4, wherein the thermostable endoglucanase is *Acidothermus cellulolyticus* E1.

7. A method for degrading lignocellulosic biomass, comprising contacting the lignocellulosic biomass with an enzyme cocktail comprising a recombinant thermostable enzyme from *Caldicellulosiruptor bescii* comprising a glycoside hydrolase (GH9) domain and a glycoside hydrolase (GH48) domain and a recombinant thermostable β glucosidase, wherein at least 50% of the cellulose in the biomass is converted to at least one sugar.

8. The method of claim 7, wherein the thermostable enzyme comprising a GH9 domain and a GH48 domain is *Caldicellulosiruptor bescii* CelA.

9. The method of claim 7, wherein the thermostable β-glucosidase is from a bacterium of the genus *Thermotoga*.

10. The method of claim 7, wherein the enzyme cocktail further comprises a thermostable endoglucanase.

11. The method of claim 10, wherein the thermostable endoglucanase is from a bacterium of the genus *Acidothermus*.

12. The method of claim 1, wherein the thermostable enzyme comprising a GH9 domain and a GH48 domain comprises at least 30% of the enzyme cocktail.

13. The method of claim 1, wherein the thermostable enzyme comprising a GH9 domain and a GH48 domain comprises at least 50% of the enzyme cocktail.

14. The method of claim 1, wherein the thermostable enzyme comprising a GH9 domain and a GH48 domain is *Caldicellulosiruptor bescii* CelA, wherein the thermostable β-glucosidase is from the bacterium *Thermotoga maritima*; and wherein the CelA comprises at least 30% of the enzyme cocktail and the β-glucosidase comprises at least about 5% of the enzyme cocktail.

15. The method of claim 14, wherein the enzyme cocktail further comprises at least 5% of the thermostable endoglucanase *Acidothermus cellulolyticus* E1.

16. A method for degrading cellulose, comprising contacting a cellulose containing material with an enzyme cocktail comprising CelA from *Caldicellulosiruptor bescii* and a thermostable β-glucosidase from *Thermotoga maritima*;
   wherein the thermostable β-glucosidase comprises about 5% of the enzyme cocktail by weight; and
   wherein at least 50% of the cellulose in the material is converted to at least one sugar.

17. The method of claim 16, wherein at least 70% of the cellulose in the material is converted to at least one sugar.

18. The method of claim 16, wherein 50 to 100% of the cellulose in the material is converted to at least one sugar.

19. The method of claim 16, wherein 70 to 100% of the cellulose in the material is converted to at least one sugar.

* * * * *

SEQUENCE LISTING

```
<160> NUMBER OF SEQ ID NOS: 10

<210> SEQ ID NO 1
<211> LENGTH: 5181
<212> TYPE: DNA
<213> ORGANISM: Caldicellulosiruptor bescii
<220> FEATURE:
<221> NAME/KEY: CDS
<222> LOCATION: (1)..(5181)
```

<400> SEQUENCE: 1

```
ggt tcg ttt aac tat ggg gaa gct tta caa aaa gct atc atg ttt tac        48
Gly Ser Phe Asn Tyr Gly Glu Ala Leu Gln Lys Ala Ile Met Phe Tyr
  1               5                  10                  15 gaa ttt caa atg tct ggt aaa ctt ccg aat tgg gta cgc aac aac tgg        96
Glu Phe Gln Met Ser Gly Lys Leu Pro Asn Trp Val Arg Asn Asn Trp
             20                  25                  30 cgt ggc gac tca gca tta aag gat ggt caa gac aat ggg ctt gat ttg       144
Arg Gly Asp Ser Ala Leu Lys Asp Gly Gln Asp Asn Gly Leu Asp Leu
         35                  40                  45 aca ggt ggt tgg ttt gac gca ggt gat cac gtc aag ttt aac ctt cca       192
Thr Gly Gly Trp Phe Asp Ala Gly Asp His Val Lys Phe Asn Leu Pro
     50                  55                  60 atg tca tac act ggt aca atg ttg tca tgg gca gtg tat gag tac aaa       240
Met Ser Tyr Thr Gly Thr Met Leu Ser Trp Ala Val Tyr Glu Tyr Lys
 65                  70                  75                  80 gat gca ttt gtc aag agt ggt caa ttg gaa cat atc tta aat caa atc       288
Asp Ala Phe Val Lys Ser Gly Gln Leu Glu His Ile Leu Asn Gln Ile
                 85                  90                  95 gaa tgg gtt aat gac tat ttt gta aaa tgt cat cca agc aaa tat gta       336
Glu Trp Val Asn Asp Tyr Phe Val Lys Cys His Pro Ser Lys Tyr Val
            100                 105                 110 tac tat tac cag gtt ggg gat gga agt aaa gat cat gca tgg tgg gga       384
Tyr Tyr Tyr Gln Val Gly Asp Gly Ser Lys Asp His Ala Trp Trp Gly
        115                 120                 125 cct gct gag gtt atg caa atg gag aga cct tca ttt aag gtc acc caa       432
Pro Ala Glu Val Met Gln Met Glu Arg Pro Ser Phe Lys Val Thr Gln
    130                 135                 140 agc agt cct gga tct aca gta gta gca gag aca gca gct tcc tta gca       480
Ser Ser Pro Gly Ser Thr Val Val Ala Glu Thr Ala Ala Ser Leu Ala
145                 150                 155                 160 gca gct tca att gtt ttg aaa gac aga aat ccc act aaa gca gca aca       528
Ala Ala Ser Ile Val Leu Lys Asp Arg Asn Pro Thr Lys Ala Ala Thr
                165                 170                 175 tat ctg caa cat gca aaa gaa tta tat gag ttt gca gaa gta aca aaa       576
Tyr Leu Gln His Ala Lys Glu Leu Tyr Glu Phe Ala Glu Val Thr Lys
            180                 185                 190 agc gat gca ggt tac act gct gca aat gga tat tac aat tca tgg agc       624
Ser Asp Ala Gly Tyr Thr Ala Ala Asn Gly Tyr Tyr Asn Ser Trp Ser
        195                 200                 205 ggt ttc tat gat gag ctt tct tgg gca gca gtt tgg ttg tat ttg gca       672
Gly Phe Tyr Asp Glu Leu Ser Trp Ala Ala Val Trp Leu Tyr Leu Ala
    210                 215                 220 aca aat gat tca aca tat ctc aca aaa gct gag tca tat gtc caa aat       720
Thr Asn Asp Ser Thr Tyr Leu Thr Lys Ala Glu Ser Tyr Val Gln Asn
225                 230                 235                 240 tgg ccc aaa att tct ggc agt aac aca att gac tac aag tgg gct cat       768
Trp Pro Lys Ile Ser Gly Ser Asn Thr Ile Asp Tyr Lys Trp Ala His
                245                 250                 255 tgc tgg gat gat gtt cac aat gga gcg gca tta ttg tta gca aaa att       816
Cys Trp Asp Asp Val His Asn Gly Ala Ala Leu Leu Leu Ala Lys Ile
            260                 265                 270 acc ggt aag gat att tat aaa caa att att gaa agt cac tta gat tac       864
Thr Gly Lys Asp Ile Tyr Lys Gln Ile Ile Glu Ser His Leu Asp Tyr
        275                 280                 285 tgg act aca gga tac aat ggc gaa agg att aag tat aca cca aaa gga       912
Trp Thr Thr Gly Tyr Asn Gly Glu Arg Ile Lys Tyr Thr Pro Lys Gly
    290                 295                 300
```

|     |     |     |     |     |     |     |     |     |     |     |     |     |     |     |     |     |
|---|---|---|---|---|---|---|---|---|---|---|---|---|---|---|---|---|
| tta | gca | tgg | ctt | gat | caa | tgg | ggt | tcg | ttg | aga | tat | gca | aca | act | aca | 960 |
| Leu | Ala | Trp | Leu | Asp | Gln | Trp | Gly | Ser | Leu | Arg | Tyr | Ala | Thr | Thr | Thr |  |
| 305 |  |  |  |  | 310 |  |  |  | 315 |  |  |  | 320 |  |  |  |

|     |     |     |     |     |     |     |     |     |     |     |     |     |     |     |     |     |
|---|---|---|---|---|---|---|---|---|---|---|---|---|---|---|---|---|
| gca | ttt | ttg | gca | ttt | gtt | tat | agc | gat | tgg | gtt | ggc | tgt | cca | agc | aca | 1008 |
| Ala | Phe | Leu | Ala | Phe | Val | Tyr | Ser | Asp | Trp | Val | Gly | Cys | Pro | Ser | Thr |  |
|  |  |  |  | 325 |  |  |  |  | 330 |  |  |  |  | 335 |  |  |

|     |     |     |     |     |     |     |     |     |     |     |     |     |     |     |     |     |
|---|---|---|---|---|---|---|---|---|---|---|---|---|---|---|---|---|
| aaa | aaa | gaa | ata | tat | aga | aaa | ttt | gga | gaa | agc | cag | att | gat | tat | gcg | 1056 |
| Lys | Lys | Glu | Ile | Tyr | Arg | Lys | Phe | Gly | Glu | Ser | Gln | Ile | Asp | Tyr | Ala |  |
|  |  |  |  | 340 |  |  |  |  | 345 |  |  |  |  | 350 |  |  |

|     |     |     |     |     |     |     |     |     |     |     |     |     |     |     |     |     |
|---|---|---|---|---|---|---|---|---|---|---|---|---|---|---|---|---|
| tta | ggc | tca | gct | gga | aga | agc | ttt | gtt | gtt | gga | ttt | ggt | aca | aat | cca | 1104 |
| Leu | Gly | Ser | Ala | Gly | Arg | Ser | Phe | Val | Val | Gly | Phe | Gly | Thr | Asn | Pro |  |
|  |  | 355 |  |  |  |  | 360 |  |  |  |  | 365 |  |  |  |  |

|     |     |     |     |     |     |     |     |     |     |     |     |     |     |     |     |     |
|---|---|---|---|---|---|---|---|---|---|---|---|---|---|---|---|---|
| cca | aag | aga | ccg | cat | cac | aga | act | gct | cat | agc | tca | tgg | gca | gac | agt | 1152 |
| Pro | Lys | Arg | Pro | His | His | Arg | Thr | Ala | His | Ser | Ser | Trp | Ala | Asp | Ser |  |
| 370 |  |  |  |  | 375 |  |  |  | 380 |  |  |  |  |  |  |  |

|     |     |     |     |     |     |     |     |     |     |     |     |     |     |     |     |     |
|---|---|---|---|---|---|---|---|---|---|---|---|---|---|---|---|---|
| cag | agt | ata | cct | tca | tat | cac | aga | cat | aca | tta | tat | gga | gcg | ctt | gtt | 1200 |
| Gln | Ser | Ile | Pro | Ser | Tyr | His | Arg | His | Thr | Leu | Tyr | Gly | Ala | Leu | Val |  |
| 385 |  |  |  |  | 390 |  |  |  |  | 395 |  |  |  |  | 400 |  |

|     |     |     |     |     |     |     |     |     |     |     |     |     |     |     |     |     |
|---|---|---|---|---|---|---|---|---|---|---|---|---|---|---|---|---|
| ggt | ggt | cca | ggc | tct | gat | gat | agc | tac | aca | gat | gat | ata | agt | aac | tat | 1248 |
| Gly | Gly | Pro | Gly | Ser | Asp | Asp | Ser | Tyr | Thr | Asp | Asp | Ile | Ser | Asn | Tyr |  |
|  |  |  |  | 405 |  |  |  |  | 410 |  |  |  |  | 415 |  |  |

|     |     |     |     |     |     |     |     |     |     |     |     |     |     |     |     |     |
|---|---|---|---|---|---|---|---|---|---|---|---|---|---|---|---|---|
| gtg | aac | aat | gag | gtt | gca | tgt | gat | tat | aat | gca | ggg | ttt | gtg | ggt | gca | 1296 |
| Val | Asn | Asn | Glu | Val | Ala | Cys | Asp | Tyr | Asn | Ala | Gly | Phe | Val | Gly | Ala |  |
|  |  |  | 420 |  |  |  |  | 425 |  |  |  |  | 430 |  |  |  |

|     |     |     |     |     |     |     |     |     |     |     |     |     |     |     |     |     |
|---|---|---|---|---|---|---|---|---|---|---|---|---|---|---|---|---|
| tta | gca | aag | atg | tat | caa | ttg | tac | ggt | ggg | aat | cca | ata | cca | gat | ttc | 1344 |
| Leu | Ala | Lys | Met | Tyr | Gln | Leu | Tyr | Gly | Gly | Asn | Pro | Ile | Pro | Asp | Phe |  |
|  |  | 435 |  |  |  |  | 440 |  |  |  |  | 445 |  |  |  |  |

|     |     |     |     |     |     |     |     |     |     |     |     |     |     |     |     |     |
|---|---|---|---|---|---|---|---|---|---|---|---|---|---|---|---|---|
| aaa | gct | att | gaa | act | cca | aca | aac | gac | gaa | ttc | ttt | gtt | gaa | gct | ggt | 1392 |
| Lys | Ala | Ile | Glu | Thr | Pro | Thr | Asn | Asp | Glu | Phe | Phe | Val | Glu | Ala | Gly |  |
|  |  | 450 |  |  |  |  | 455 |  |  |  |  | 460 |  |  |  |  |

|     |     |     |     |     |     |     |     |     |     |     |     |     |     |     |     |     |
|---|---|---|---|---|---|---|---|---|---|---|---|---|---|---|---|---|
| ata | aat | gca | tcc | gga | act | aac | ttt | att | gaa | att | aaa | gcg | ata | gtt | aat | 1440 |
| Ile | Asn | Ala | Ser | Gly | Thr | Asn | Phe | Ile | Glu | Ile | Lys | Ala | Ile | Val | Asn |  |
| 465 |  |  |  |  | 470 |  |  |  |  | 475 |  |  |  |  | 480 |  |

|     |     |     |     |     |     |     |     |     |     |     |     |     |     |     |     |     |
|---|---|---|---|---|---|---|---|---|---|---|---|---|---|---|---|---|
| aac | caa | agt | ggt | tgg | cct | gcc | aga | gca | aca | gat | aag | ctt | aaa | ttt | aga | 1488 |
| Asn | Gln | Ser | Gly | Trp | Pro | Ala | Arg | Ala | Thr | Asp | Lys | Leu | Lys | Phe | Arg |  |
|  |  |  |  | 485 |  |  |  |  | 490 |  |  |  |  | 495 |  |  |

|     |     |     |     |     |     |     |     |     |     |     |     |     |     |     |     |     |
|---|---|---|---|---|---|---|---|---|---|---|---|---|---|---|---|---|
| tat | ttt | gtt | gac | ctg | agt | gaa | tta | att | aaa | gca | gga | tat | tca | cca | aat | 1536 |
| Tyr | Phe | Val | Asp | Leu | Ser | Glu | Leu | Ile | Lys | Ala | Gly | Tyr | Ser | Pro | Asn |  |
|  |  |  | 500 |  |  |  |  | 505 |  |  |  |  | 510 |  |  |  |

|     |     |     |     |     |     |     |     |     |     |     |     |     |     |     |     |     |
|---|---|---|---|---|---|---|---|---|---|---|---|---|---|---|---|---|
| caa | tta | acc | ttg | agc | acc | aat | tat | aat | caa | ggt | gca | aaa | gta | agt | gga | 1584 |
| Gln | Leu | Thr | Leu | Ser | Thr | Asn | Tyr | Asn | Gln | Gly | Ala | Lys | Val | Ser | Gly |  |
|  |  |  |  | 515 |  |  |  |  | 520 |  |  |  |  | 525 |  |  |

|     |     |     |     |     |     |     |     |     |     |     |     |     |     |     |     |     |
|---|---|---|---|---|---|---|---|---|---|---|---|---|---|---|---|---|
| cct | tat | gta | tgg | gat | gca | agc | aaa | aat | ata | tac | tac | att | tta | gta | gac | 1632 |
| Pro | Tyr | Val | Trp | Asp | Ala | Ser | Lys | Asn | Ile | Tyr | Tyr | Ile | Leu | Val | Asp |  |
|  | 530 |  |  |  |  | 535 |  |  |  |  | 540 |  |  |  |  |  |

|     |     |     |     |     |     |     |     |     |     |     |     |     |     |     |     |     |
|---|---|---|---|---|---|---|---|---|---|---|---|---|---|---|---|---|
| ttt | act | ggc | aca | ttg | att | tat | cca | ggt | ggt | caa | gac | aaa | tat | aag | aaa | 1680 |
| Phe | Thr | Gly | Thr | Leu | Ile | Tyr | Pro | Gly | Gly | Gln | Asp | Lys | Tyr | Lys | Lys |  |
| 545 |  |  |  |  | 550 |  |  |  |  | 555 |  |  |  |  | 560 |  |

|     |     |     |     |     |     |     |     |     |     |     |     |     |     |     |     |     |
|---|---|---|---|---|---|---|---|---|---|---|---|---|---|---|---|---|
| gaa | gtc | caa | ttc | aga | att | gca | gca | cca | cag | aat | gta | cag | tgg | gat | aat | 1728 |
| Glu | Val | Gln | Phe | Arg | Ile | Ala | Ala | Pro | Gln | Asn | Val | Gln | Trp | Asp | Asn |  |
|  |  |  |  | 565 |  |  |  |  | 570 |  |  |  |  | 575 |  |  |

|     |     |     |     |     |     |     |     |     |     |     |     |     |     |     |     |     |
|---|---|---|---|---|---|---|---|---|---|---|---|---|---|---|---|---|
| tct | aac | gac | tat | tct | ttc | cag | gat | ata | aag | gga | gtt | tca | agt | ggt | tca | 1776 |
| Ser | Asn | Asp | Tyr | Ser | Phe | Gln | Asp | Ile | Lys | Gly | Val | Ser | Ser | Gly | Ser |  |
|  |  |  | 580 |  |  |  |  | 585 |  |  |  |  | 590 |  |  |  |

|     |     |     |     |     |     |     |     |     |     |     |     |     |     |     |     |     |
|---|---|---|---|---|---|---|---|---|---|---|---|---|---|---|---|---|
| gtt | gtt | aaa | act | aaa | tat | att | cca | ctt | tat | gat | gga | gat | gtg | aaa | gta | 1824 |
| Val | Val | Lys | Thr | Lys | Tyr | Ile | Pro | Leu | Tyr | Asp | Gly | Asp | Val | Lys | Val |  |
|  |  | 595 |  |  |  |  | 600 |  |  |  |  | 605 |  |  |  |  |

|     |     |     |     |     |     |     |     |     |     |     |     |     |     |     |     |     |
|---|---|---|---|---|---|---|---|---|---|---|---|---|---|---|---|---|
| tgg | ggt | gaa | gaa | cca | gga | act | tct | gga | gca | aca | ccg | aca | cca | aca | gca | 1872 |
| Trp | Gly | Glu | Glu | Pro | Gly | Thr | Ser | Gly | Ala | Thr | Pro | Thr | Pro | Thr | Ala |  |
| 610 |  |  |  |  | 615 |  |  |  |  | 620 |  |  |  |  |  |  |

```
                                                        -continued
aca gca aca cca aca cca acg ccg aca gta aca cca aca ccg act cca        1920
Thr Ala Thr Pro Thr Pro Thr Pro Thr Val Thr Pro Thr Pro Thr Pro
625                 630                 635                 640 aca cca aca tca act gct aca cca aca ccg aca cca aca ccg aca gta        1968
Thr Pro Thr Ser Thr Ala Thr Pro Thr Pro Thr Pro Thr Pro Thr Val
            645                 650                 655 aca cca acc ccg act ccg aca ccg act gct aca cca aca gca acg cca        2016
Thr Pro Thr Pro Thr Pro Thr Pro Thr Ala Thr Pro Thr Ala Thr Pro
        660                 665                 670 aca cca aca tcg acg ccg agc agc aca cct gta gca ggt gga cag ata        2064
Thr Pro Thr Ser Thr Pro Ser Ser Thr Pro Val Ala Gly Gly Gln Ile
    675                 680                 685 aag gta ttg tat gct aac aag gag aca aat agc aca act aat acg ata        2112
Lys Val Leu Tyr Ala Asn Lys Glu Thr Asn Ser Thr Thr Asn Thr Ile
690                 695                 700 agg cca tgg ttg aag gta gtg aac act gga agc agc agc ata gat ttg        2160
Arg Pro Trp Leu Lys Val Val Asn Thr Gly Ser Ser Ser Ile Asp Leu
705                 710                 715                 720 agc agg gta acg ata agg tac tgg tac acg gta gat ggg gac aag gca        2208
Ser Arg Val Thr Ile Arg Tyr Trp Tyr Thr Val Asp Gly Asp Lys Ala
            725                 730                 735 cag agt gcg ata tca gac tgg gca cag ata gga gca agc aat gtg aca        2256
Gln Ser Ala Ile Ser Asp Trp Ala Gln Ile Gly Ala Ser Asn Val Thr
        740                 745                 750 ttc aag ttt gtg aag ctg agc agt agc gta agt gga gcg gac tat tat        2304
Phe Lys Phe Val Lys Leu Ser Ser Ser Val Ser Gly Ala Asp Tyr Tyr
    755                 760                 765 tta gag ata gga ttt aag agt gga gct ggg cag ttg cag gct ggc aaa        2352
Leu Glu Ile Gly Phe Lys Ser Gly Ala Gly Gln Leu Gln Ala Gly Lys
770                 775                 780 gac aca ggg gag ata cag ata agg ttt aac aag agt gat tgg agc aat        2400
Asp Thr Gly Glu Ile Gln Ile Arg Phe Asn Lys Ser Asp Trp Ser Asn
785                 790                 795                 800 tac aat cag ggg aat gac tgg tca tgg atg cag agc atg acg aat tat        2448
Tyr Asn Gln Gly Asn Asp Trp Ser Trp Met Gln Ser Met Thr Asn Tyr
            805                 810                 815 gga gag aat gtg aag gta aca gcg tat ata gat ggt gta ttg gta tgg        2496
Gly Glu Asn Val Lys Val Thr Ala Tyr Ile Asp Gly Val Leu Val Trp
        820                 825                 830 gga cag gag ccg agt gga gcg aca cca aca ccg aca gcg aca cca gca        2544
Gly Gln Glu Pro Ser Gly Ala Thr Pro Thr Pro Thr Ala Thr Pro Ala
    835                 840                 845 ccg aca gtg aca ccg aca cct aca cca aca cca acg tca aca cca act        2592
Pro Thr Val Thr Pro Thr Pro Thr Pro Thr Pro Thr Ser Thr Pro Thr
850                 855                 860 gct aca cca aca gca acg cca aca cca aca ccg acg ccg agc agc aca        2640
Ala Thr Pro Thr Ala Thr Pro Thr Pro Thr Pro Thr Pro Ser Ser Thr
865                 870                 875                 880 cct gta gca ggc ggg cag ata aag gta ttg tat gct aac aag gag aca        2688
Pro Val Ala Gly Gly Gln Ile Lys Val Leu Tyr Ala Asn Lys Glu Thr
            885                 890                 895 aat agc aca aca aac acg ata agg cca tgg ttg aag gta gtg aac act        2736
Asn Ser Thr Thr Asn Thr Ile Arg Pro Trp Leu Lys Val Val Asn Thr
        900                 905                 910 gga agc agc agc ata gat ttg agc agg gta acg ata agg tac tgg tac        2784
Gly Ser Ser Ser Ile Asp Leu Ser Arg Val Thr Ile Arg Tyr Trp Tyr
    915                 920                 925 acg gta gat ggg gac aag gca cag agt gcg ata tca gac tgg gca cag        2832
Thr Val Asp Gly Asp Lys Ala Gln Ser Ala Ile Ser Asp Trp Ala Gln
930                 935                 940
```

```
ata gga gca agc aat gtg aca ttc aag ttt gtg aag ctg agc agt agc   2880
Ile Gly Ala Ser Asn Val Thr Phe Lys Phe Val Lys Leu Ser Ser Ser
945                 950                 955                 960 gta agt gga gcg gac tat tat tta gag ata gga ttt aag agt gga gct   2928
Val Ser Gly Ala Asp Tyr Tyr Leu Glu Ile Gly Phe Lys Ser Gly Ala
                965                 970                 975 ggg cag ttg cag gct ggt aaa gac aca ggg gag ata cag ata agg ttt   2976
Gly Gln Leu Gln Ala Gly Lys Asp Thr Gly Glu Ile Gln Ile Arg Phe
            980                 985                 990 aac aag agt gac tgg agc aat tac aat cag ggg aat gac tgg tca tgg   3024
Asn Lys Ser Asp Trp Ser Asn Tyr Asn Gln Gly Asn Asp Trp Ser Trp
        995                 1000                1005 atg cag agc atg acg aat tat gga gag aat gtg aag gta aca gcg       3069
Met Gln Ser Met Thr Asn Tyr Gly Glu Asn Val Lys Val Thr Ala
    1010                1015                1020 tat ata gat ggt gta ttg gta tgg gga cag gag ccg agt gga gcg       3114
Tyr Ile Asp Gly Val Leu Val Trp Gly Gln Glu Pro Ser Gly Ala
    1025                1030                1035 aca cca aca ccg aca gcg aca cca gca ccg aca gtg aca ccg aca       3159
Thr Pro Thr Pro Thr Ala Thr Pro Ala Pro Thr Val Thr Pro Thr
    1040                1045                1050 cct aca cca gca cca act cca acc ccg aca cca aca cca act gct       3204
Pro Thr Pro Ala Pro Thr Pro Thr Pro Thr Pro Thr Pro Thr Ala
    1055                1060                1065 aca cca aca cca acg cca aca cca acc cca acc gcg aca cca aca       3249
Thr Pro Thr Pro Thr Pro Thr Pro Thr Pro Thr Ala Thr Pro Thr
    1070                1075                1080 gta aca gca aca cca aca ccg acg ccg agc agc aca ccg agt gtg       3294
Val Thr Ala Thr Pro Thr Pro Thr Pro Ser Ser Thr Pro Ser Val
    1085                1090                1095 ctt ggc gaa tat ggg cag agg ttt atg tgg tta tgg aac aag ata       3339
Leu Gly Glu Tyr Gly Gln Arg Phe Met Trp Leu Trp Asn Lys Ile
    1100                1105                1110 cat gat cct gcg aac ggg tat ttt aac cag gat ggg ata cca tat       3384
His Asp Pro Ala Asn Gly Tyr Phe Asn Gln Asp Gly Ile Pro Tyr
    1115                1120                1125 cat tcg gta gag aca ttg ata tgc gaa gca cct gat tat ggt cat       3429
His Ser Val Glu Thr Leu Ile Cys Glu Ala Pro Asp Tyr Gly His
    1130                1135                1140 ttg acc acg agt gag gca ttt tcg tac tat gta tgg tta gag gca       3474
Leu Thr Thr Ser Glu Ala Phe Ser Tyr Tyr Val Trp Leu Glu Ala
    1145                1150                1155 gtg tat ggt aag tta acg ggt gac tgg agc aaa ttt aag aca gca       3519
Val Tyr Gly Lys Leu Thr Gly Asp Trp Ser Lys Phe Lys Thr Ala
    1160                1165                1170 tgg gac aca tta gag aag tat atg ata cca tca gcg gaa gat cag       3564
Trp Asp Thr Leu Glu Lys Tyr Met Ile Pro Ser Ala Glu Asp Gln
    1175                1180                1185 ccg atg agg tca tat gat cct aac aag cca gcg aca tac gca ggg       3609
Pro Met Arg Ser Tyr Asp Pro Asn Lys Pro Ala Thr Tyr Ala Gly
    1190                1195                1200 gag tgg gag aca ccg gac aag tat cca tcg ccg ttg gag ttt aat       3654
Glu Trp Glu Thr Pro Asp Lys Tyr Pro Ser Pro Leu Glu Phe Asn
    1205                1210                1215 gta cct gtt ggc aaa gac ccg ttg cat aat gaa ctt gtg agc aca       3699
Val Pro Val Gly Lys Asp Pro Leu His Asn Glu Leu Val Ser Thr
    1220                1225                1230 tat ggt agc aca tta atg tat ggt atg cac tgg ttg atg gac gta       3744
Tyr Gly Ser Thr Leu Met Tyr Gly Met His Trp Leu Met Asp Val
    1235                1240                1245
```

-continued

| | | | | | | | | | | | | | | |
|---|---|---|---|---|---|---|---|---|---|---|---|---|---|---|
| gac | aac | tgg | tat | gga | tat | ggc | aag | aga | ggg | gac | gga | gta | agt | cgg | 3789 |
| Asp | Asn | Trp | Tyr | Gly | Tyr | Gly | Lys | Arg | Gly | Asp | Gly | Val | Ser | Arg | |
| | 1250 | | | | 1255 | | | | 1260 | | | | | | |
| gca | tca | ttt | atc | aac | acg | ttc | cag | aga | ggg | cct | gag | gag | tct | gta | 3834 |
| Ala | Ser | Phe | Ile | Asn | Thr | Phe | Gln | Arg | Gly | Pro | Glu | Glu | Ser | Val | |
| 1265 | | | | | 1270 | | | | | 1275 | | | | | |
| tgg | gag | acg | gtg | ccg | cat | ccg | agc | tgg | gag | gaa | ttc | aag | tgg | ggc | 3879 |
| Trp | Glu | Thr | Val | Pro | His | Pro | Ser | Trp | Glu | Glu | Phe | Lys | Trp | Gly | |
| 1280 | | | | | 1285 | | | | | 1290 | | | | | |
| gga | ccg | aat | gga | ttt | tta | gat | ttg | ttt | att | aag | gat | cag | aac | tat | 3924 |
| Gly | Pro | Asn | Gly | Phe | Leu | Asp | Leu | Phe | Ile | Lys | Asp | Gln | Asn | Tyr | |
| 1295 | | | | | 1300 | | | | | 1305 | | | | | |
| tcg | aag | cag | tgg | aga | tat | acg | gat | gca | cca | gat | gct | gat | gcg | aga | 3969 |
| Ser | Lys | Gln | Trp | Arg | Tyr | Thr | Asp | Ala | Pro | Asp | Ala | Asp | Ala | Arg | |
| 1310 | | | | | 1315 | | | | | 1320 | | | | | |
| gct | att | cag | gct | act | tat | tgg | gcg | aaa | gta | tgg | gcg | aag | gag | caa | 4014 |
| Ala | Ile | Gln | Ala | Thr | Tyr | Trp | Ala | Lys | Val | Trp | Ala | Lys | Glu | Gln | |
| 1325 | | | | | 1330 | | | | | 1335 | | | | | |
| ggt | aag | ttt | aat | gag | ata | agc | agc | tat | gta | gcg | aag | gca | gcg | aag | 4059 |
| Gly | Lys | Phe | Asn | Glu | Ile | Ser | Ser | Tyr | Val | Ala | Lys | Ala | Ala | Lys | |
| 1340 | | | | | 1345 | | | | | 1350 | | | | | |
| atg | gga | gac | tat | tta | agg | tat | gcg | atg | ttt | gac | aag | tat | ttc | aag | 4104 |
| Met | Gly | Asp | Tyr | Leu | Arg | Tyr | Ala | Met | Phe | Asp | Lys | Tyr | Phe | Lys | |
| 1355 | | | | | 1360 | | | | | 1365 | | | | | |
| cca | tta | gga | tgt | cag | gat | aag | aat | gcg | gct | gga | gga | acg | ggg | tat | 4149 |
| Pro | Leu | Gly | Cys | Gln | Asp | Lys | Asn | Ala | Ala | Gly | Gly | Thr | Gly | Tyr | |
| 1370 | | | | | 1375 | | | | | 1380 | | | | | |
| gac | agt | gca | cat | tat | ctg | cta | tca | tgg | tat | tat | gca | tgg | ggt | gga | 4194 |
| Asp | Ser | Ala | His | Tyr | Leu | Leu | Ser | Trp | Tyr | Tyr | Ala | Trp | Gly | Gly | |
| 1385 | | | | | 1390 | | | | | 1395 | | | | | |
| gca | ttg | gat | gga | gca | tgg | tca | tgg | aag | ata | ggg | agc | agc | cat | gtg | 4239 |
| Ala | Leu | Asp | Gly | Ala | Trp | Ser | Trp | Lys | Ile | Gly | Ser | Ser | His | Val | |
| 1400 | | | | | 1405 | | | | | 1410 | | | | | |
| cac | ttt | gga | tat | cag | aat | ccg | atg | gcg | gca | tgg | gca | tta | gcg | aat | 4284 |
| His | Phe | Gly | Tyr | Gln | Asn | Pro | Met | Ala | Ala | Trp | Ala | Leu | Ala | Asn | |
| 1415 | | | | | 1420 | | | | | 1425 | | | | | |
| gat | agt | gat | atg | aag | ccg | aag | tcg | ccg | aat | gga | gcg | agt | gac | tgg | 4329 |
| Asp | Ser | Asp | Met | Lys | Pro | Lys | Ser | Pro | Asn | Gly | Ala | Ser | Asp | Trp | |
| 1430 | | | | | 1435 | | | | | 1440 | | | | | |
| gca | aag | agt | ttg | aag | agg | cag | ata | gaa | ttt | tac | agg | tgg | tta | cag | 4374 |
| Ala | Lys | Ser | Leu | Lys | Arg | Gln | Ile | Glu | Phe | Tyr | Arg | Trp | Leu | Gln | |
| 1445 | | | | | 1450 | | | | | 1455 | | | | | |
| tca | gcg | gag | gga | gcg | ata | gca | gga | ggc | gcg | aca | aat | tca | tgg | aat | 4419 |
| Ser | Ala | Glu | Gly | Ala | Ile | Ala | Gly | Gly | Ala | Thr | Asn | Ser | Trp | Asn | |
| 1460 | | | | | 1465 | | | | | 1470 | | | | | |
| ggc | aga | tat | gag | aag | tat | cca | gca | ggg | aca | gca | aca | ttt | tat | gga | 4464 |
| Gly | Arg | Tyr | Glu | Lys | Tyr | Pro | Ala | Gly | Thr | Ala | Thr | Phe | Tyr | Gly | |
| 1475 | | | | | 1480 | | | | | 1485 | | | | | |
| atg | gca | tat | gaa | ccg | aat | ccg | gta | tat | cat | gat | cct | ggg | agc | aac | 4509 |
| Met | Ala | Tyr | Glu | Pro | Asn | Pro | Val | Tyr | His | Asp | Pro | Gly | Ser | Asn | |
| 1490 | | | | | 1495 | | | | | 1500 | | | | | |
| aca | tgg | ttt | gga | ttc | cag | gca | tgg | tcg | atg | cag | agg | gta | gcg | gag | 4554 |
| Thr | Trp | Phe | Gly | Phe | Gln | Ala | Trp | Ser | Met | Gln | Arg | Val | Ala | Glu | |
| 1505 | | | | | 1510 | | | | | 1515 | | | | | |
| tat | tac | tat | gtg | aca | gga | gat | aag | gac | gca | gga | gca | ctg | ctt | gag | 4599 |
| Tyr | Tyr | Tyr | Val | Thr | Gly | Asp | Lys | Asp | Ala | Gly | Ala | Leu | Leu | Glu | |
| 1520 | | | | | 1525 | | | | | 1530 | | | | | |
| aag | tgg | gta | agc | tgg | gtt | aag | agt | gta | gtg | aag | ttg | aat | agt | gat | 4644 |
| Lys | Trp | Val | Ser | Trp | Val | Lys | Ser | Val | Val | Lys | Leu | Asn | Ser | Asp | |
| 1535 | | | | | 1540 | | | | | 1545 | | | | | |

| | | | | | | | | | | | |
|---|---|---|---|---|---|---|---|---|---|---|---|
| ggt | acg | ttt | gcg | ata | ccg | tcg | acg | ctt | gat | tgg | agc | gga | caa | cct | 4689 |
| Gly | Thr | Phe | Ala | Ile | Pro | Ser | Thr | Leu | Asp | Trp | Ser | Gly | Gln | Pro | |
| | 1550 | | | | 1555 | | | | | 1560 | | | | | |

| gat | aca | tgg | aac | ggg | gcg | tat | aca | ggg | aat | agc | aac | tta | cat | gtt | 4734 |
| Asp | Thr | Trp | Asn | Gly | Ala | Tyr | Thr | Gly | Asn | Ser | Asn | Leu | His | Val |
| 1565 | | | | | 1570 | | | | | 1575 | | | | |

| aag | gta | gtg | gac | tat | ggt | act | gac | tta | gga | ata | aca | gcg | tca | ttg | 4779 |
| Lys | Val | Val | Asp | Tyr | Gly | Thr | Asp | Leu | Gly | Ile | Thr | Ala | Ser | Leu |
| 1580 | | | | | 1585 | | | | | 1590 | | | | |

| gcg | aat | gcg | ttg | ttg | tac | tat | agt | gca | ggg | acg | aag | aag | tat | ggg | 4824 |
| Ala | Asn | Ala | Leu | Leu | Tyr | Tyr | Ser | Ala | Gly | Thr | Lys | Lys | Tyr | Gly |
| 1595 | | | | | 1600 | | | | | 1605 | | | | |

| gta | ttt | gat | gag | gga | gcg | aag | aat | tta | gcg | aag | gaa | ttg | ctg | gac | 4869 |
| Val | Phe | Asp | Glu | Gly | Ala | Lys | Asn | Leu | Ala | Lys | Glu | Leu | Leu | Asp |
| 1610 | | | | | 1615 | | | | | 1620 | | | | |

| agg | atg | tgg | aag | ttg | tac | agg | gat | gag | aag | gga | ttg | tca | gcg | cca | 4914 |
| Arg | Met | Trp | Lys | Leu | Tyr | Arg | Asp | Glu | Lys | Gly | Leu | Ser | Ala | Pro |
| 1625 | | | | | 1630 | | | | | 1635 | | | | |

| gag | aag | aga | gcg | gac | tac | aag | agg | ttc | ttt | gag | caa | gag | gta | tat | 4959 |
| Glu | Lys | Arg | Ala | Asp | Tyr | Lys | Arg | Phe | Phe | Glu | Gln | Glu | Val | Tyr |
| 1640 | | | | | 1645 | | | | | 1650 | | | | |

| ata | ccg | gca | gga | tgg | ata | ggg | aag | atg | ccg | aat | gga | gat | gta | ata | 5004 |
| Ile | Pro | Ala | Gly | Trp | Ile | Gly | Lys | Met | Pro | Asn | Gly | Asp | Val | Ile |
| 1655 | | | | | 1660 | | | | | 1665 | | | | |

| aag | agt | gga | gtt | aag | ttt | ata | gac | ata | agg | agc | aag | tat | aaa | caa | 5049 |
| Lys | Ser | Gly | Val | Lys | Phe | Ile | Asp | Ile | Arg | Ser | Lys | Tyr | Lys | Gln |
| 1670 | | | | | 1675 | | | | | 1680 | | | | |

| gat | cct | gat | tgg | ccg | aag | tta | gag | gcg | gca | tac | aag | tca | ggg | cag | 5094 |
| Asp | Pro | Asp | Trp | Pro | Lys | Leu | Glu | Ala | Ala | Tyr | Lys | Ser | Gly | Gln |
| 1685 | | | | | 1690 | | | | | 1695 | | | | |

| gca | cct | gag | ttc | aga | tat | cac | agg | ttc | tgg | gca | cag | tgc | gac | ata | 5139 |
| Ala | Pro | Glu | Phe | Arg | Tyr | His | Arg | Phe | Trp | Ala | Gln | Cys | Asp | Ile |
| 1700 | | | | | 1705 | | | | | 1710 | | | | |

| gca | ata | gct | aat | gca | aca | tat | gaa | ata | ctg | ttt | ggc | aat | caa | | 5181 |
| Ala | Ile | Ala | Asn | Ala | Thr | Tyr | Glu | Ile | Leu | Phe | Gly | Asn | Gln | |
| 1715 | | | | | 1720 | | | | | 1725 | | | | |

<210> SEQ ID NO 2
<211> LENGTH: 1727
<212> TYPE: PRT
<213> ORGANISM: Caldicellulosiruptor bescii

<400> SEQUENCE: 2

Gly Ser Phe Asn Tyr Gly Glu Ala Leu Gln Lys Ala Ile Met Phe Tyr
1               5                   10                  15

Glu Phe Gln Met Ser Gly Lys Leu Pro Asn Trp Val Arg Asn Asn Trp
            20                  25                  30

Arg Gly Asp Ser Ala Leu Lys Asp Gly Gln Asp Asn Gly Leu Asp Leu
        35                  40                  45

Thr Gly Gly Trp Phe Asp Ala Gly Asp His Val Lys Phe Asn Leu Pro
    50                  55                  60

Met Ser Tyr Thr Gly Thr Met Leu Ser Trp Ala Val Tyr Glu Tyr Lys
65                  70                  75                  80

Asp Ala Phe Val Lys Ser Gly Gln Leu Glu His Ile Leu Asn Gln Ile
                85                  90                  95

Glu Trp Val Asn Asp Tyr Phe Val Lys Cys His Pro Ser Lys Tyr Val
            100                 105                 110

Tyr Tyr Tyr Gln Val Gly Asp Gly Ser Lys Asp His Ala Trp Trp Gly
        115                 120                 125

```
Pro Ala Glu Val Met Gln Met Glu Arg Pro Ser Phe Lys Val Thr Gln
    130                 135                 140
Ser Ser Pro Gly Ser Thr Val Ala Glu Thr Ala Ala Ser Leu Ala
145                 150                 155                 160
Ala Ala Ser Ile Val Leu Lys Asp Arg Asn Pro Thr Lys Ala Ala Thr
                165                 170                 175
Tyr Leu Gln His Ala Lys Glu Leu Tyr Glu Phe Ala Glu Val Thr Lys
                180                 185                 190
Ser Asp Ala Gly Tyr Thr Ala Ala Asn Gly Tyr Tyr Asn Ser Trp Ser
                195                 200                 205
Gly Phe Tyr Asp Glu Leu Ser Trp Ala Ala Val Trp Leu Tyr Leu Ala
210                 215                 220
Thr Asn Asp Ser Thr Tyr Leu Thr Lys Ala Glu Ser Tyr Val Gln Asn
225                 230                 235                 240
Trp Pro Lys Ile Ser Gly Ser Asn Thr Ile Asp Tyr Lys Trp Ala His
                245                 250                 255
Cys Trp Asp Asp Val His Asn Gly Ala Ala Leu Leu Leu Ala Lys Ile
                260                 265                 270
Thr Gly Lys Asp Ile Tyr Lys Gln Ile Ile Glu Ser His Leu Asp Tyr
                275                 280                 285
Trp Thr Thr Gly Tyr Asn Gly Glu Arg Ile Lys Tyr Thr Pro Lys Gly
290                 295                 300
Leu Ala Trp Leu Asp Gln Trp Gly Ser Leu Arg Tyr Ala Thr Thr Thr
305                 310                 315                 320
Ala Phe Leu Ala Phe Val Tyr Ser Asp Trp Val Gly Cys Pro Ser Thr
                325                 330                 335
Lys Lys Glu Ile Tyr Arg Lys Phe Gly Glu Ser Gln Ile Asp Tyr Ala
                340                 345                 350
Leu Gly Ser Ala Gly Arg Ser Phe Val Val Gly Phe Gly Thr Asn Pro
                355                 360                 365
Pro Lys Arg Pro His His Arg Thr Ala His Ser Ser Trp Ala Asp Ser
370                 375                 380
Gln Ser Ile Pro Ser Tyr His Arg His Thr Leu Tyr Gly Ala Leu Val
385                 390                 395                 400
Gly Gly Pro Gly Ser Asp Asp Ser Tyr Thr Asp Asp Ile Ser Asn Tyr
                405                 410                 415
Val Asn Asn Glu Val Ala Cys Asp Tyr Asn Ala Gly Phe Val Gly Ala
                420                 425                 430
Leu Ala Lys Met Tyr Gln Leu Tyr Gly Gly Asn Pro Ile Pro Asp Phe
                435                 440                 445
Lys Ala Ile Glu Thr Pro Thr Asn Asp Glu Phe Phe Val Glu Ala Gly
                450                 455                 460
Ile Asn Ala Ser Gly Thr Asn Phe Ile Glu Ile Lys Ala Ile Val Asn
465                 470                 475                 480
Asn Gln Ser Gly Trp Pro Ala Arg Ala Thr Asp Lys Leu Lys Phe Arg
                485                 490                 495
Tyr Phe Val Asp Leu Ser Glu Leu Ile Lys Ala Gly Tyr Ser Pro Asn
                500                 505                 510
Gln Leu Thr Leu Ser Thr Asn Tyr Asn Gln Gly Ala Lys Val Ser Gly
                515                 520                 525
Pro Tyr Val Trp Asp Ala Ser Lys Asn Ile Tyr Tyr Ile Leu Val Asp
530                 535                 540
```

-continued

Phe Thr Gly Thr Leu Ile Tyr Pro Gly Gly Gln Asp Lys Tyr Lys Lys
545                 550                 555                 560

Glu Val Gln Phe Arg Ile Ala Ala Pro Gln Asn Val Gln Trp Asp Asn
            565                 570                 575

Ser Asn Asp Tyr Ser Phe Gln Asp Ile Lys Gly Val Ser Ser Gly Ser
                580                 585                 590

Val Val Lys Thr Lys Tyr Ile Pro Leu Tyr Asp Gly Asp Val Lys Val
            595                 600                 605

Trp Gly Glu Glu Pro Gly Thr Ser Gly Ala Thr Pro Thr Pro Thr Ala
610                 615                 620

Thr Ala Thr Pro Thr Pro Thr Pro Thr Val Thr Pro Thr Pro Thr Pro
625                 630                 635                 640

Thr Pro Thr Ser Thr Ala Thr Pro Thr Pro Thr Pro Thr Pro Thr Val
            645                 650                 655

Thr Pro Thr Pro Thr Pro Thr Pro Thr Ala Thr Pro Thr Ala Thr Pro
                660                 665                 670

Thr Pro Thr Ser Thr Pro Ser Ser Thr Pro Val Ala Gly Gly Gln Ile
            675                 680                 685

Lys Val Leu Tyr Ala Asn Lys Glu Thr Asn Ser Thr Thr Asn Thr Ile
690                 695                 700

Arg Pro Trp Leu Lys Val Asn Thr Gly Ser Ser Ile Asp Leu
705                 710                 715                 720

Ser Arg Val Thr Ile Arg Tyr Trp Tyr Thr Val Asp Gly Asp Lys Ala
                725                 730                 735

Gln Ser Ala Ile Ser Asp Trp Ala Gln Ile Gly Ala Ser Asn Val Thr
            740                 745                 750

Phe Lys Phe Val Lys Leu Ser Ser Val Ser Gly Ala Asp Tyr Tyr
            755                 760                 765

Leu Glu Ile Gly Phe Lys Ser Gly Ala Gly Gln Leu Gln Ala Gly Lys
770                 775                 780

Asp Thr Gly Glu Ile Gln Ile Arg Phe Asn Lys Ser Asp Trp Ser Asn
785                 790                 795                 800

Tyr Asn Gln Gly Asn Asp Trp Ser Trp Met Gln Ser Met Thr Asn Tyr
            805                 810                 815

Gly Glu Asn Val Lys Val Thr Ala Tyr Ile Asp Gly Val Leu Val Trp
            820                 825                 830

Gly Gln Glu Pro Ser Gly Ala Thr Pro Thr Pro Thr Ala Thr Pro Ala
            835                 840                 845

Pro Thr Val Thr Pro Thr Pro Thr Pro Thr Pro Thr Ser Thr Pro Thr
850                 855                 860

Ala Thr Pro Thr Ala Thr Pro Thr Pro Thr Pro Thr Pro Ser Ser Thr
865                 870                 875                 880

Pro Val Ala Gly Gly Gln Ile Lys Val Leu Tyr Ala Asn Lys Glu Thr
            885                 890                 895

Asn Ser Thr Thr Asn Thr Ile Arg Pro Trp Leu Lys Val Val Asn Thr
                900                 905                 910

Gly Ser Ser Ile Asp Leu Ser Arg Val Thr Ile Arg Tyr Trp Tyr
            915                 920                 925

Thr Val Asp Gly Asp Lys Ala Gln Ser Ala Ile Ser Asp Trp Ala Gln
            930                 935                 940

Ile Gly Ala Ser Asn Val Thr Phe Lys Phe Val Lys Leu Ser Ser Ser
945                 950                 955                 960

```
Val Ser Gly Ala Asp Tyr Tyr Leu Glu Ile Gly Phe Lys Ser Gly Ala
            965                 970                 975
Gly Gln Leu Gln Ala Gly Lys Asp Thr Gly Glu Ile Gln Ile Arg Phe
        980                 985                 990
Asn Lys Ser Asp Trp Ser Asn Tyr Asn Gln Gly Asn Asp Trp Ser Trp
        995                 1000                1005
Met Gln Ser Met Thr Asn Tyr Gly Glu Asn Val Lys Val Thr Ala
    1010                1015                1020
Tyr Ile Asp Gly Val Leu Val Trp Gly Gln Glu Pro Ser Gly Ala
    1025                1030                1035
Thr Pro Thr Pro Thr Ala Thr Pro Ala Pro Thr Val Thr Pro Thr
    1040                1045                1050
Pro Thr Pro Ala Pro Thr Pro Thr Pro Thr Pro Thr Pro Thr Ala
    1055                1060                1065
Thr Pro Thr Pro Thr Pro Thr Pro Thr Pro Thr Ala Thr Pro Thr
    1070                1075                1080
Val Thr Ala Thr Pro Thr Pro Thr Pro Ser Ser Thr Pro Ser Val
    1085                1090                1095
Leu Gly Glu Tyr Gly Gln Arg Phe Met Trp Leu Trp Asn Lys Ile
    1100                1105                1110
His Asp Pro Ala Asn Gly Tyr Phe Asn Gln Asp Gly Ile Pro Tyr
    1115                1120                1125
His Ser Val Glu Thr Leu Ile Cys Glu Ala Pro Asp Tyr Gly His
    1130                1135                1140
Leu Thr Thr Ser Glu Ala Phe Ser Tyr Tyr Val Trp Leu Glu Ala
    1145                1150                1155
Val Tyr Gly Lys Leu Thr Gly Asp Trp Ser Lys Phe Lys Thr Ala
    1160                1165                1170
Trp Asp Thr Leu Glu Lys Tyr Met Ile Pro Ser Ala Glu Asp Gln
    1175                1180                1185
Pro Met Arg Ser Tyr Asp Pro Asn Lys Pro Ala Thr Tyr Ala Gly
    1190                1195                1200
Glu Trp Glu Thr Pro Asp Lys Tyr Pro Ser Pro Leu Glu Phe Asn
    1205                1210                1215
Val Pro Val Gly Lys Asp Pro Leu His Asn Glu Leu Val Ser Thr
    1220                1225                1230
Tyr Gly Ser Thr Leu Met Tyr Gly Met His Trp Leu Met Asp Val
    1235                1240                1245
Asp Asn Trp Tyr Gly Tyr Gly Lys Arg Gly Asp Gly Val Ser Arg
    1250                1255                1260
Ala Ser Phe Ile Asn Thr Phe Gln Arg Gly Pro Glu Glu Ser Val
    1265                1270                1275
Trp Glu Thr Val Pro His Pro Ser Trp Glu Glu Phe Lys Trp Gly
    1280                1285                1290
Gly Pro Asn Gly Phe Leu Asp Leu Phe Ile Lys Asp Gln Asn Tyr
    1295                1300                1305
Ser Lys Gln Trp Arg Tyr Thr Asp Ala Pro Asp Ala Asp Ala Arg
    1310                1315                1320
Ala Ile Gln Ala Thr Tyr Trp Ala Lys Val Trp Ala Lys Glu Gln
    1325                1330                1335
Gly Lys Phe Asn Glu Ile Ser Ser Tyr Val Ala Lys Ala Ala Lys
    1340                1345                1350
```

```
Met Gly Asp Tyr Leu Arg Tyr Ala Met Phe Asp Lys Tyr Phe Lys
1355                1360                1365

Pro Leu Gly Cys Gln Asp Lys Asn Ala Ala Gly Gly Thr Gly Tyr
1370                1375                1380

Asp Ser Ala His Tyr Leu Leu Ser Trp Tyr Tyr Ala Trp Gly Gly
1385                1390                1395

Ala Leu Asp Gly Ala Trp Ser Trp Lys Ile Gly Ser Ser His Val
1400                1405                1410

His Phe Gly Tyr Gln Asn Pro Met Ala Ala Trp Ala Leu Ala Asn
1415                1420                1425

Asp Ser Asp Met Lys Pro Lys Ser Pro Asn Gly Ala Ser Asp Trp
1430                1435                1440

Ala Lys Ser Leu Lys Arg Gln Ile Glu Phe Tyr Arg Trp Leu Gln
1445                1450                1455

Ser Ala Glu Gly Ala Ile Ala Gly Gly Ala Thr Asn Ser Trp Asn
1460                1465                1470

Gly Arg Tyr Glu Lys Tyr Pro Ala Gly Thr Ala Thr Phe Tyr Gly
1475                1480                1485

Met Ala Tyr Glu Pro Asn Pro Val Tyr His Asp Pro Gly Ser Asn
1490                1495                1500

Thr Trp Phe Gly Phe Gln Ala Trp Ser Met Gln Arg Val Ala Glu
1505                1510                1515

Tyr Tyr Tyr Val Thr Gly Asp Lys Asp Ala Gly Ala Leu Leu Glu
1520                1525                1530

Lys Trp Val Ser Trp Val Lys Ser Val Val Lys Leu Asn Ser Asp
1535                1540                1545

Gly Thr Phe Ala Ile Pro Ser Thr Leu Asp Trp Ser Gly Gln Pro
1550                1555                1560

Asp Thr Trp Asn Gly Ala Tyr Thr Gly Asn Ser Asn Leu His Val
1565                1570                1575

Lys Val Val Asp Tyr Gly Thr Asp Leu Gly Ile Thr Ala Ser Leu
1580                1585                1590

Ala Asn Ala Leu Leu Tyr Tyr Ser Ala Gly Thr Lys Lys Tyr Gly
1595                1600                1605

Val Phe Asp Glu Gly Ala Lys Asn Leu Ala Lys Glu Leu Leu Asp
1610                1615                1620

Arg Met Trp Lys Leu Tyr Arg Asp Glu Lys Gly Leu Ser Ala Pro
1625                1630                1635

Glu Lys Arg Ala Asp Tyr Lys Arg Phe Phe Glu Gln Glu Val Tyr
1640                1645                1650

Ile Pro Ala Gly Trp Ile Gly Lys Met Pro Asn Gly Asp Val Ile
1655                1660                1665

Lys Ser Gly Val Lys Phe Ile Asp Ile Arg Ser Lys Tyr Lys Gln
1670                1675                1680

Asp Pro Asp Trp Pro Lys Leu Glu Ala Ala Tyr Lys Ser Gly Gln
1685                1690                1695

Ala Pro Glu Phe Arg Tyr His Arg Phe Trp Ala Gln Cys Asp Ile
1700                1705                1710

Ala Ile Ala Asn Ala Thr Tyr Glu Ile Leu Phe Gly Asn Gln
1715                1720                1725
```

```
<210> SEQ ID NO 3
<211> LENGTH: 1338
<212> TYPE: DNA
<213> ORGANISM: Thermotoga maritima
<220> FEATURE:
<221> NAME/KEY: CDS
<222> LOCATION: (1)..(1338)

<400> SEQUENCE: 3
```

| | | | | | | | | | | | | | | | | |
|---|---|---|---|---|---|---|---|---|---|---|---|---|---|---|---|---|
| atg | aac | gtg | aaa | aag | ttc | cct | gaa | gga | ttc | ctc | tgg | ggt | gtt | gca | aca | 48 |
| Met | Asn | Val | Lys | Lys | Phe | Pro | Glu | Gly | Phe | Leu | Trp | Gly | Val | Ala | Thr | |
| 1 | | | | 5 | | | | | 10 | | | | | 15 | | |
| gct | tcc | tac | cag | atc | gag | ggt | tct | ccc | ctc | gca | gac | gga | gct | ggt | atg | 96 |
| Ala | Ser | Tyr | Gln | Ile | Glu | Gly | Ser | Pro | Leu | Ala | Asp | Gly | Ala | Gly | Met | |
| | | | 20 | | | | | 25 | | | | | 30 | | | |
| tct | atc | tgg | cac | acc | ttc | tcc | cat | act | cct | gga | aat | gta | aag | aac | ggt | 144 |
| Ser | Ile | Trp | His | Thr | Phe | Ser | His | Thr | Pro | Gly | Asn | Val | Lys | Asn | Gly | |
| | | 35 | | | | | 40 | | | | | 45 | | | | |
| gac | acg | gga | gat | gtg | gcc | tgc | gac | cac | tac | aac | aga | tgg | aaa | gag | gac | 192 |
| Asp | Thr | Gly | Asp | Val | Ala | Cys | Asp | His | Tyr | Asn | Arg | Trp | Lys | Glu | Asp | |
| | 50 | | | | | 55 | | | | | 60 | | | | | |
| att | gaa | atc | ata | gag | aaa | ctc | gga | gta | aag | gct | tac | aga | ttt | tca | atc | 240 |
| Ile | Glu | Ile | Ile | Glu | Lys | Leu | Gly | Val | Lys | Ala | Tyr | Arg | Phe | Ser | Ile | |
| 65 | | | | | 70 | | | | | 75 | | | | | 80 | |
| agc | tgg | cca | aga | ata | ctt | ccg | gaa | gga | aca | gga | agg | gtg | aat | cag | aaa | 288 |
| Ser | Trp | Pro | Arg | Ile | Leu | Pro | Glu | Gly | Thr | Gly | Arg | Val | Asn | Gln | Lys | |
| | | | | 85 | | | | | 90 | | | | | 95 | | |
| gga | ctg | gat | ttt | tac | aac | agg | atc | ata | gac | acc | ctg | ctg | gaa | aaa | ggt | 336 |
| Gly | Leu | Asp | Phe | Tyr | Asn | Arg | Ile | Ile | Asp | Thr | Leu | Leu | Glu | Lys | Gly | |
| | | | 100 | | | | | 105 | | | | | 110 | | | |
| atc | aca | ccc | ttt | gtg | acc | atc | tat | cac | tgg | gat | ctt | ccc | ttc | gct | ctt | 384 |
| Ile | Thr | Pro | Phe | Val | Thr | Ile | Tyr | His | Trp | Asp | Leu | Pro | Phe | Ala | Leu | |
| | | 115 | | | | | 120 | | | | | 125 | | | | |
| cag | ctg | aaa | gga | gga | tgg | gcg | aac | aga | gaa | ata | gcg | gat | tgg | ttc | gca | 432 |
| Gln | Leu | Lys | Gly | Gly | Trp | Ala | Asn | Arg | Glu | Ile | Ala | Asp | Trp | Phe | Ala | |
| | 130 | | | | | 135 | | | | | 140 | | | | | |
| gaa | tac | tca | agg | gtt | ctc | ttt | gaa | aat | ttc | ggt | gat | cgt | gtg | aag | aac | 480 |
| Glu | Tyr | Ser | Arg | Val | Leu | Phe | Glu | Asn | Phe | Gly | Asp | Arg | Val | Lys | Asn | |
| 145 | | | | | 150 | | | | | 155 | | | | | 160 | |
| tgg | atc | acc | ttg | aac | gaa | ccg | tgg | gtt | gtt | gcc | ata | gtg | ggg | cat | ctg | 528 |
| Trp | Ile | Thr | Leu | Asn | Glu | Pro | Trp | Val | Val | Ala | Ile | Val | Gly | His | Leu | |
| | | | | 165 | | | | | 170 | | | | | 175 | | |
| tac | gga | gtc | cac | gct | cct | gga | atg | aga | gat | att | tac | gtg | gct | ttc | cga | 576 |
| Tyr | Gly | Val | His | Ala | Pro | Gly | Met | Arg | Asp | Ile | Tyr | Val | Ala | Phe | Arg | |
| | | | 180 | | | | | 185 | | | | | 190 | | | |
| gct | gtt | cac | aat | ctc | ttg | agg | gca | cac | gcc | aga | gcg | gtg | aaa | gtg | ttc | 624 |
| Ala | Val | His | Asn | Leu | Leu | Arg | Ala | His | Ala | Arg | Ala | Val | Lys | Val | Phe | |
| | | 195 | | | | | 200 | | | | | 205 | | | | |
| agg | gaa | acc | gtg | aaa | gat | gga | aag | atc | gga | ata | gtt | ttc | aac | aat | gga | 672 |
| Arg | Glu | Thr | Val | Lys | Asp | Gly | Lys | Ile | Gly | Ile | Val | Phe | Asn | Asn | Gly | |
| | 210 | | | | | 215 | | | | | 220 | | | | | |
| tat | ttc | gaa | cct | gcg | agt | gaa | aaa | gaa | gaa | gac | atc | aga | gcg | gtg | aga | 720 |
| Tyr | Phe | Glu | Pro | Ala | Ser | Glu | Lys | Glu | Glu | Asp | Ile | Arg | Ala | Val | Arg | |
| 225 | | | | | 230 | | | | | 235 | | | | | 240 | |
| ttc | atg | cat | cag | ttc | aac | aac | tat | cct | ctc | ttt | ctc | aat | ccg | atc | tac | 768 |
| Phe | Met | His | Gln | Phe | Asn | Asn | Tyr | Pro | Leu | Phe | Leu | Asn | Pro | Ile | Tyr | |
| | | | | 245 | | | | | 250 | | | | | 255 | | |
| aga | gga | gat | tac | ccg | gag | ctc | gtt | ctg | gaa | ttt | gcc | aga | gag | tat | cta | 816 |
| Arg | Gly | Asp | Tyr | Pro | Glu | Leu | Val | Leu | Glu | Phe | Ala | Arg | Glu | Tyr | Leu | |
| | | | 260 | | | | | 265 | | | | | 270 | | | |

```
ccg gag aat tac aaa gat gac atg tcc gag ata cag gaa aag atc gac      864
Pro Glu Asn Tyr Lys Asp Asp Met Ser Glu Ile Gln Glu Lys Ile Asp
        275                 280                 285 ttt gtt gga ttg aac tat tac tcc ggt cat ttg gtg aag ttc gat cca      912
Phe Val Gly Leu Asn Tyr Tyr Ser Gly His Leu Val Lys Phe Asp Pro
    290                 295                 300 gat gca cca gct aag gtc tct ttc gtt gaa agg gat ctt cca aaa aca      960
Asp Ala Pro Ala Lys Val Ser Phe Val Glu Arg Asp Leu Pro Lys Thr
305                 310                 315                 320 gcc atg gga tgg gag atc gtt cca gaa gga atc tac tgg atc ctg aag     1008
Ala Met Gly Trp Glu Ile Val Pro Glu Gly Ile Tyr Trp Ile Leu Lys
                325                 330                 335 aag gtg aaa gaa gaa tac aac cca cca gag gtt tac atc aca gag aat     1056
Lys Val Lys Glu Glu Tyr Asn Pro Pro Glu Val Tyr Ile Thr Glu Asn
            340                 345                 350 ggg gct gct ttt gac gac gta gtt agt gaa gat gga aga gtt cac gat     1104
Gly Ala Ala Phe Asp Asp Val Val Ser Glu Asp Gly Arg Val His Asp
        355                 360                 365 caa aac aga atc gat tat ttg aag gcc cac att ggt cag gca tgg aag     1152
Gln Asn Arg Ile Asp Tyr Leu Lys Ala His Ile Gly Gln Ala Trp Lys
    370                 375                 380 gcc ata cag gag gga gtg ccg ctt aaa ggt tac ttc gtc tgg tcg ctc     1200
Ala Ile Gln Glu Gly Val Pro Leu Lys Gly Tyr Phe Val Trp Ser Leu
385                 390                 395                 400 ctc gac aat ttc gaa tgg gca gag gga tat tcc aag aga ttt ggt att     1248
Leu Asp Asn Phe Glu Trp Ala Glu Gly Tyr Ser Lys Arg Phe Gly Ile
                405                 410                 415 gtg tat gta gac tac agc act caa aaa cgc atc gta aaa gac agt ggg     1296
Val Tyr Val Asp Tyr Ser Thr Gln Lys Arg Ile Val Lys Asp Ser Gly
            420                 425                 430 tac tgg tac tcg aat gtg gtt aaa aac aac ggt ctg gaa gac             1338
Tyr Trp Tyr Ser Asn Val Val Lys Asn Asn Gly Leu Glu Asp
        435                 440                 445

<210> SEQ ID NO 4
<211> LENGTH: 446
<212> TYPE: PRT
<213> ORGANISM: Thermotoga maritima

<400> SEQUENCE: 4

Met Asn Val Lys Lys Phe Pro Glu Gly Phe Leu Trp Gly Val Ala Thr
1               5                   10                  15

Ala Ser Tyr Gln Ile Glu Gly Ser Pro Leu Ala Asp Gly Ala Gly Met
            20                  25                  30

Ser Ile Trp His Thr Phe Ser His Thr Pro Gly Asn Val Lys Asn Gly
        35                  40                  45

Asp Thr Gly Asp Val Ala Cys Asp His Tyr Asn Arg Trp Lys Glu Asp
    50                  55                  60

Ile Glu Ile Ile Glu Lys Leu Gly Val Lys Ala Tyr Arg Phe Ser Ile
65                  70                  75                  80

Ser Trp Pro Arg Ile Leu Pro Glu Gly Thr Gly Arg Val Asn Gln Lys
                85                  90                  95

Gly Leu Asp Phe Tyr Asn Arg Ile Ile Asp Thr Leu Leu Glu Lys Gly
            100                 105                 110

Ile Thr Pro Phe Val Thr Ile Tyr His Trp Asp Leu Pro Phe Ala Leu
        115                 120                 125

Gln Leu Lys Gly Gly Trp Ala Asn Arg Glu Ile Ala Asp Trp Phe Ala
    130                 135                 140
```

```
Glu Tyr Ser Arg Val Leu Phe Glu Asn Phe Gly Asp Arg Val Lys Asn
145                 150                 155                 160

Trp Ile Thr Leu Asn Glu Pro Trp Val Ala Ile Val Gly His Leu
            165                 170                 175

Tyr Gly Val His Ala Pro Gly Met Arg Asp Ile Tyr Val Ala Phe Arg
        180                 185                 190

Ala Val His Asn Leu Leu Arg Ala His Ala Arg Ala Val Lys Val Phe
    195                 200                 205

Arg Glu Thr Val Lys Asp Gly Lys Ile Gly Ile Val Phe Asn Asn Gly
    210                 215                 220

Tyr Phe Glu Pro Ala Ser Glu Lys Glu Asp Ile Arg Ala Val Arg
225                 230                 235                 240

Phe Met His Gln Phe Asn Asn Tyr Pro Leu Phe Leu Asn Pro Ile Tyr
                245                 250                 255

Arg Gly Asp Tyr Pro Glu Leu Val Leu Glu Phe Ala Arg Glu Tyr Leu
            260                 265                 270

Pro Glu Asn Tyr Lys Asp Asp Met Ser Glu Ile Gln Glu Lys Ile Asp
        275                 280                 285

Phe Val Gly Leu Asn Tyr Tyr Ser Gly His Leu Val Lys Phe Asp Pro
290                 295                 300

Asp Ala Pro Ala Lys Val Ser Phe Val Glu Arg Asp Leu Pro Lys Thr
305                 310                 315                 320

Ala Met Gly Trp Glu Ile Val Pro Glu Gly Ile Tyr Trp Ile Leu Lys
                325                 330                 335

Lys Val Lys Glu Glu Tyr Asn Pro Pro Glu Val Tyr Ile Thr Glu Asn
            340                 345                 350

Gly Ala Ala Phe Asp Asp Val Val Ser Glu Asp Gly Arg Val His Asp
        355                 360                 365

Gln Asn Arg Ile Asp Tyr Leu Lys Ala His Ile Gly Gln Ala Trp Lys
    370                 375                 380

Ala Ile Gln Glu Gly Val Pro Leu Lys Gly Tyr Phe Val Trp Ser Leu
385                 390                 395                 400

Leu Asp Asn Phe Glu Trp Ala Glu Gly Tyr Ser Lys Arg Phe Gly Ile
                405                 410                 415

Val Tyr Val Asp Tyr Ser Thr Gln Lys Arg Ile Val Lys Asp Ser Gly
            420                 425                 430

Tyr Trp Tyr Ser Asn Val Val Lys Asn Asn Gly Leu Glu Asp
        435                 440                 445

<210> SEQ ID NO 5
<211> LENGTH: 1686
<212> TYPE: DNA
<213> ORGANISM: Acidothermus cellulolyticus
<220> FEATURE:
<221> NAME/KEY: CDS
<222> LOCATION: (1)..(1686)

<400> SEQUENCE: 5 gtg ccg cgc gca ttg cgg cga gtg cct ggc tcg cgg gtg atg ctg cgg      48
Val Pro Arg Ala Leu Arg Arg Val Pro Gly Ser Arg Val Met Leu Arg
1               5                   10                  15 gtc ggc gtc gtc gtc gcg gtg ctg gca ttg gtt gcc gca ctc gcc aac      96
Val Gly Val Val Val Ala Val Leu Ala Leu Val Ala Ala Leu Ala Asn
            20                  25                  30 cta gcc gtg ccg cgg ccg gct cgc gcc gcg ggc ggc ggc tat tgg cac      144
Leu Ala Val Pro Arg Pro Ala Arg Ala Ala Gly Gly Gly Tyr Trp His
        35                  40                  45
```

-continued

| | | |
|---|---|---|
| acg agc ggc cgg gag atc ctg gac gcg aac aac gtg ccg gta cgg atc<br>Thr Ser Gly Arg Glu Ile Leu Asp Ala Asn Asn Val Pro Val Arg Ile<br>50           55                  60 | 192 |
| gcc ggc atc aac tgg ttt ggg ttc gaa acc tgc aat tac gtc gtg cac<br>Ala Gly Ile Asn Trp Phe Gly Phe Glu Thr Cys Asn Tyr Val Val His<br>65              70                 75                  80 | 240 |
| ggt ctc tgg tca cgc gac tac cgc agc atg ctc gac cag ata aag tcg<br>Gly Leu Trp Ser Arg Asp Tyr Arg Ser Met Leu Asp Gln Ile Lys Ser<br>                85                 90                 95 | 288 |
| ctc ggc tac aac aca atc cgg ctg ccg tac tct gac gac att ctc aag<br>Leu Gly Tyr Asn Thr Ile Arg Leu Pro Tyr Ser Asp Asp Ile Leu Lys<br>               100                105                110 | 336 |
| ccg ggc acc atg ccg aac agc atc aat ttt tac cag atg aat cag gac<br>Pro Gly Thr Met Pro Asn Ser Ile Asn Phe Tyr Gln Met Asn Gln Asp<br>               115                120                125 | 384 |
| ctg cag ggt ctg acg tcc ttg cag gtc atg gac aaa atc gtc gcg tac<br>Leu Gln Gly Leu Thr Ser Leu Gln Val Met Asp Lys Ile Val Ala Tyr<br>130                135                140 | 432 |
| gcc ggt cag atc ggc ctg cgc atc att ctt gac cgc cac cga ccg gat<br>Ala Gly Gln Ile Gly Leu Arg Ile Ile Leu Asp Arg His Arg Pro Asp<br>145                150                155                160 | 480 |
| tgc agc ggg cag tcg gcg ctg tgg tac acg agc agc gtc tcg gag gct<br>Cys Ser Gly Gln Ser Ala Leu Trp Tyr Thr Ser Ser Val Ser Glu Ala<br>                165                170                175 | 528 |
| acg tgg att tcc gac ctg caa gcg ctg gcg cag cgc tac aag gga aac<br>Thr Trp Ile Ser Asp Leu Gln Ala Leu Ala Gln Arg Tyr Lys Gly Asn<br>                180                185                190 | 576 |
| ccg acg gtc gtc ggc ttt gac ttg cac aac gag ccg cat gac ccg gcc<br>Pro Thr Val Val Gly Phe Asp Leu His Asn Glu Pro His Asp Pro Ala<br>                195                200                205 | 624 |
| tgc tgg ggc tgc ggc gat ccg agc atc gac tgg cga ttg gcc gcc gag<br>Cys Trp Gly Cys Gly Asp Pro Ser Ile Asp Trp Arg Leu Ala Ala Glu<br>210                215                220 | 672 |
| cgg gcc gga aac gcc gtg ctc tcg gtg aat ccg aac ctg ctc att ttc<br>Arg Ala Gly Asn Ala Val Leu Ser Val Asn Pro Asn Leu Leu Ile Phe<br>225                230                235                240 | 720 |
| gtc gaa ggt gtg cag agc tac aac gga gac tcc tac tgg tgg ggc ggc<br>Val Glu Gly Val Gln Ser Tyr Asn Gly Asp Ser Tyr Trp Trp Gly Gly<br>                245                250                255 | 768 |
| aac ctg caa gga gcc ggc cag tac ccg gtc gtg ctg aac gtg ccg aac<br>Asn Leu Gln Gly Ala Gly Gln Tyr Pro Val Val Leu Asn Val Pro Asn<br>                260                265                270 | 816 |
| cgc ctg gtg tac tcg gcg cac gac tac gcg acg agc gtc tac ccg cag<br>Arg Leu Val Tyr Ser Ala His Asp Tyr Ala Thr Ser Val Tyr Pro Gln<br>                275                280                285 | 864 |
| acg tgg ttc agc gat ccg acc ttc ccc aac aac atg ccc ggc atc tgg<br>Thr Trp Phe Ser Asp Pro Thr Phe Pro Asn Asn Met Pro Gly Ile Trp<br>                290                295                300 | 912 |
| aac aag aac tgg gga tac ctc ttc aat cag aac att gca ccg gta tgg<br>Asn Lys Asn Trp Gly Tyr Leu Phe Asn Gln Asn Ile Ala Pro Val Trp<br>305                310                315                320 | 960 |
| ctg ggc gaa ttc ggt acg aca ctg caa tcc acg acc gac cag acg tgg<br>Leu Gly Glu Phe Gly Thr Thr Leu Gln Ser Thr Thr Asp Gln Thr Trp<br>                325                330                335 | 1008 |
| ctg aag acg ctc gtc cag tac cta cgg ccg acc gcg caa tac ggt gcg<br>Leu Lys Thr Leu Val Gln Tyr Leu Arg Pro Thr Ala Gln Tyr Gly Ala<br>                340                345                350 | 1056 |
| gac agc ttc cag tgg acc ttc tgg tcc tgg aac ccc gat tcc ggc gac<br>Asp Ser Phe Gln Trp Thr Phe Trp Ser Trp Asn Pro Asp Ser Gly Asp<br>                355                360                365 | 1104 |

```
aca gga gga att ctc aag gat gac tgg cag acg gtc gac aca gta aaa     1152
Thr Gly Gly Ile Leu Lys Asp Asp Trp Gln Thr Val Asp Thr Val Lys
        370                 375                 380 gac ggc tat ctc gcg ccg atc aag tcg tcg att ttc gat cct gtc ggc     1200
Asp Gly Tyr Leu Ala Pro Ile Lys Ser Ser Ile Phe Asp Pro Val Gly
385                 390                 395                 400 gcg tct gca tcg cct agc agt caa ccg tcc ccg tcg gtg tcg ccg tct     1248
Ala Ser Ala Ser Pro Ser Ser Gln Pro Ser Pro Ser Val Ser Pro Ser
                405                 410                 415 ccg tcg ccg agc ccg tcg gcg agt cgg acg ccg acg cct act ccg acg     1296
Pro Ser Pro Ser Pro Ser Ala Ser Arg Thr Pro Thr Pro Thr Pro Thr
            420                 425                 430 ccg aca gcc agc ccg acg cca acg ctg acc cct act gct acg ccc acg     1344
Pro Thr Ala Ser Pro Thr Pro Thr Leu Thr Pro Thr Ala Thr Pro Thr
        435                 440                 445 ccc acg gca agc ccg acg ccg tca ccg acg gca gcc tcc gga gcc cgc     1392
Pro Thr Ala Ser Pro Thr Pro Ser Pro Thr Ala Ala Ser Gly Ala Arg
    450                 455                 460 tgc acc gcg agt tac cag gtc aac agc gat tgg ggc aat ggc ttc acg     1440
Cys Thr Ala Ser Tyr Gln Val Asn Ser Asp Trp Gly Asn Gly Phe Thr
465                 470                 475                 480 gta acg gtg gcc gtg aca aat tcc gga tcc gtc gcg acc aag aca tgg     1488
Val Thr Val Ala Val Thr Asn Ser Gly Ser Val Ala Thr Lys Thr Trp
                485                 490                 495 acg gtc agt tgg aca ttc ggc gga aat cag acg att acc aat tcg tgg     1536
Thr Val Ser Trp Thr Phe Gly Gly Asn Gln Thr Ile Thr Asn Ser Trp
            500                 505                 510 aat gca gcg gtc acg cag aac ggt cag tcg gta acg gct cgg aat atg     1584
Asn Ala Ala Val Thr Gln Asn Gly Gln Ser Val Thr Ala Arg Asn Met
        515                 520                 525 agt tat aac aac gtg att cag cct ggt cag aac acc acg ttc gga ttc     1632
Ser Tyr Asn Asn Val Ile Gln Pro Gly Gln Asn Thr Thr Phe Gly Phe
    530                 535                 540 cag gcg agc tat acc gga agc aac gcg gca ccg aca gtc gcc tgc gca     1680
Gln Ala Ser Tyr Thr Gly Ser Asn Ala Ala Pro Thr Val Ala Cys Ala
545                 550                 555                 560 gca agt                                                              1686
Ala Ser <210> SEQ ID NO 6
<211> LENGTH: 562
<212> TYPE: PRT
<213> ORGANISM: Acidothermus cellulolyticus

<400> SEQUENCE: 6

Val Pro Arg Ala Leu Arg Arg Val Pro Gly Ser Arg Val Met Leu Arg
1               5                   10                  15

Val Gly Val Val Val Ala Val Leu Ala Leu Val Ala Ala Leu Ala Asn
                20                  25                  30

Leu Ala Val Pro Arg Pro Ala Arg Ala Ala Gly Gly Gly Tyr Trp His
            35                  40                  45

Thr Ser Gly Arg Glu Ile Leu Asp Ala Asn Asn Val Pro Val Arg Ile
        50                  55                  60

Ala Gly Ile Asn Trp Phe Gly Phe Glu Thr Cys Asn Tyr Val Val His
65                  70                  75                  80

Gly Leu Trp Ser Arg Asp Tyr Arg Ser Met Leu Asp Gln Ile Lys Ser
                85                  90                  95

Leu Gly Tyr Asn Thr Ile Arg Leu Pro Tyr Ser Asp Asp Ile Leu Lys
            100                 105                 110
```

```
Pro Gly Thr Met Pro Asn Ser Ile Asn Phe Tyr Gln Met Asn Gln Asp
            115                 120                 125

Leu Gln Gly Leu Thr Ser Leu Gln Val Met Asp Lys Ile Val Ala Tyr
    130                 135                 140

Ala Gly Gln Ile Gly Leu Arg Ile Ile Leu Asp Arg His Arg Pro Asp
145                 150                 155                 160

Cys Ser Gly Gln Ser Ala Leu Trp Tyr Thr Ser Val Ser Glu Ala
                165                 170                 175

Thr Trp Ile Ser Asp Leu Gln Ala Leu Ala Gln Arg Tyr Lys Gly Asn
                180                 185                 190

Pro Thr Val Val Gly Phe Asp Leu His Asn Glu Pro His Asp Pro Ala
            195                 200                 205

Cys Trp Gly Cys Gly Asp Pro Ser Ile Asp Trp Arg Leu Ala Ala Glu
    210                 215                 220

Arg Ala Gly Asn Ala Val Leu Ser Val Asn Pro Asn Leu Leu Ile Phe
225                 230                 235                 240

Val Glu Gly Val Gln Ser Tyr Asn Gly Asp Ser Tyr Trp Trp Gly Gly
                245                 250                 255

Asn Leu Gln Gly Ala Gly Gln Tyr Pro Val Val Leu Asn Val Pro Asn
            260                 265                 270

Arg Leu Val Tyr Ser Ala His Asp Tyr Ala Thr Ser Val Tyr Pro Gln
    275                 280                 285

Thr Trp Phe Ser Asp Pro Thr Phe Pro Asn Asn Met Pro Gly Ile Trp
    290                 295                 300

Asn Lys Asn Trp Gly Tyr Leu Phe Asn Gln Asn Ile Ala Pro Val Trp
305                 310                 315                 320

Leu Gly Glu Phe Gly Thr Thr Leu Gln Ser Thr Thr Asp Gln Thr Trp
                325                 330                 335

Leu Lys Thr Leu Val Gln Tyr Leu Arg Pro Thr Ala Gln Tyr Gly Ala
            340                 345                 350

Asp Ser Phe Gln Trp Thr Phe Trp Ser Trp Asn Pro Asp Ser Gly Asp
    355                 360                 365

Thr Gly Gly Ile Leu Lys Asp Asp Trp Gln Thr Val Asp Thr Val Lys
    370                 375                 380

Asp Gly Tyr Leu Ala Pro Ile Lys Ser Ser Ile Phe Asp Pro Val Gly
385                 390                 395                 400

Ala Ser Ala Ser Pro Ser Ser Gln Pro Ser Pro Val Ser Pro Ser
                405                 410                 415

Pro Ser Pro Ser Pro Ser Ala Ser Arg Thr Pro Thr Pro Thr Pro Thr
                420                 425                 430

Pro Thr Ala Ser Pro Thr Pro Thr Leu Thr Pro Thr Ala Thr Pro Thr
            435                 440                 445

Pro Thr Ala Ser Pro Thr Pro Ser Pro Thr Ala Ala Ser Gly Ala Arg
            450                 455                 460

Cys Thr Ala Ser Tyr Gln Val Asn Ser Asp Trp Gly Asn Gly Phe Thr
465                 470                 475                 480

Val Thr Val Ala Val Thr Asn Ser Gly Ser Val Ala Thr Lys Thr Trp
                485                 490                 495

Thr Val Ser Trp Thr Phe Gly Gly Asn Gln Thr Ile Thr Asn Ser Trp
            500                 505                 510

Asn Ala Ala Val Thr Gln Asn Gly Gln Ser Val Thr Ala Arg Asn Met
            515                 520                 525
```

```
Ser Tyr Asn Asn Val Ile Gln Pro Gly Gln Asn Thr Thr Phe Gly Phe
    530                 535                 540

Gln Ala Ser Tyr Thr Gly Ser Asn Ala Ala Pro Thr Val Ala Cys Ala
545                 550                 555                 560

Ala Ser

<210> SEQ ID NO 7
<211> LENGTH: 32
<212> TYPE: DNA
<213> ORGANISM: Artificial Sequence
<220> FEATURE:
<223> OTHER INFORMATION: PCR Primer

<400> SEQUENCE: 7
acaccggcta gcagcagcac acctgtagca gg                              32

<210> SEQ ID NO 8
<211> LENGTH: 32
<212> TYPE: DNA
<213> ORGANISM: Artificial Sequence
<220> FEATURE:
<223> OTHER INFORMATION: PCR Primer

<400> SEQUENCE: 8
tagcttctcg agttattgat tgccaaacag ta                              32

<210> SEQ ID NO 9
<211> LENGTH: 32
<212> TYPE: DNA
<213> ORGANISM: Artificial Sequence
<220> FEATURE:
<223> OTHER INFORMATION: PCR Primer

<400> SEQUENCE: 9
atgctagcta gcggttcgtt taactatggg ga                              32

<210> SEQ ID NO 10
<211> LENGTH: 35
<212> TYPE: DNA
<213> ORGANISM: Artificial Sequence
<220> FEATURE:
<223> OTHER INFORMATION: PCR Primer

<400> SEQUENCE: 10
gtcgttctcg agtcattcaa tagctttgaa atctg                           35
```